(12) United States Patent
Tojo et al.

(10) Patent No.: US 12,161,437 B2
(45) Date of Patent: Dec. 10, 2024

(54) SURGICAL ROBOT, SURGICAL SYSTEM, AND CONTROL METHOD

(71) Applicants: KAWASAKI JUKOGYO KABUSHIKI KAISHA, Kobe (JP); MEDICAROID CORPORATION, Kobe (JP)

(72) Inventors: Tsuyoshi Tojo, Kobe (JP); Nobuyasu Shimomura, Kobe (JP); Tetsuo Ichii, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 302 days.

(21) Appl. No.: 17/782,209

(22) PCT Filed: Dec. 4, 2020

(86) PCT No.: PCT/JP2020/045269
§ 371 (c)(1),
(2) Date: Jun. 3, 2022

(87) PCT Pub. No.: WO2021/112228
PCT Pub. Date: Jun. 10, 2021

(65) Prior Publication Data
US 2023/0012535 A1    Jan. 19, 2023

(30) Foreign Application Priority Data

Dec. 5, 2019  (JP) ................................. 2019-220692

(51) Int. Cl.
| | | |
|---|---|---|
| A61B 34/37 | (2016.01) | |
| A61B 34/00 | (2016.01) | |
| A61B 34/30 | (2016.01) | |

(52) U.S. Cl.
CPC ........ *A61B 34/37* (2016.02); *A61B 2034/304* (2016.02); *A61B 2034/306* (2016.02); *A61B 34/70* (2016.02)

(58) Field of Classification Search
CPC ... A61B 34/37; A61B 34/70; A61B 2034/304; A61B 2034/306; A61B 90/361; A61B 2090/067; A61B 90/50; B25J 9/0087; B25J 9/06
See application file for complete search history.

(56) References Cited

U.S. PATENT DOCUMENTS

2018/0271732 A1*  9/2018  Yano ...................... A61G 13/04

FOREIGN PATENT DOCUMENTS

| EP | 3520729 A1 | 8/2019 |
|---|---|---|
| JP | H08-107898 A | 4/1996 |
| JP | 2019-529051 A | 10/2019 |

* cited by examiner

*Primary Examiner* — Ian Jen
*Assistant Examiner* — Renee LaRose
(74) *Attorney, Agent, or Firm* — METROLEX IP LAW GROUP, PLLC; Robert L. Scott, Esq

(57) ABSTRACT

A surgical robot includes robot arms, an arm base, and a control device. Each of the robot arms includes a base portion, a tip portion that can hold a medical instrument, and links. The link adjacent to the base portion is connected to the base portion through a rotational joint. The control device controls the robot arm having at least seven degrees of freedom among the robot arms such that when viewed from a direction parallel to an axial direction of a rotation axis of the rotational joint, a first portion of a first link is located between a second portion of the base portion and a third portion of the tip portion.

18 Claims, 12 Drawing Sheets

SURGICAL ROBOT, SURGICAL SYSTEM, AND CONTROL METHOD

CROSS-REFERENCE TO RELATED APPLICATION

This application claims priority to and the benefit of Japanese Patent Application No. 2019-220692 filed on Dec. 5, 2019, the entire disclosure of which is incorporated herein by reference.

TECHNICAL FIELD

The present disclosure relates to a surgical robot, a surgical system, and a control method.

BACKGROUND ART

Robots have been used to assist surgery. For example, PTL 1 discloses a surgical robot system including manipulators. The manipulators include robot arms and surgery instruments coupled to the robot arms.

CITATION LIST

Patent Literature

PTL 1: Published Japanese Translation of PCT Application No. 2019-529051

SUMMARY OF INVENTION

Technical Problem

In the surgical robot system of PTL 1, the manipulators are arranged adjacent to each other along a circular-arc member. Therefore, there is a possibility that when the robot arm of the manipulator is operated so as to be bent, the robot arm is brought into contact with the adjacent manipulator.

An object of the present disclosure is to provide a surgical robot, a surgical system, and a control method, each of which prevents a robot arm from contacting peripheral objects, such as an adjacent robot arm, during operation.

Solution to Problem

To achieve the above object, a surgical robot according to one aspect of the present disclosure includes: robot arms each having plural degrees of freedom; an elongated arm base that holds base end portions of the robot arms; and a control device that controls movements of the robot arms. Each of the robot arms includes a base portion, a tip portion that holds a medical instrument, and links that couple the base portion and the tip portion and are coupled to each other. The link adjacent to the base portion is connected to the base portion through a rotational joint. At least one of the robot arms has at least seven degrees of freedom. The control device controls one robot arm having the at least seven degrees of freedom such that when viewed from a direction parallel to an axial direction of a rotation axis of the rotational joint, a first portion of a first link that is one of the links is located between a second portion of the base portion and a third portion of the tip portion.

According to the technology of the present disclosure, the robot arm is prevented from contacting peripheral objects during operation.

DESCRIPTION OF EMBODIMENTS

Figure 1:
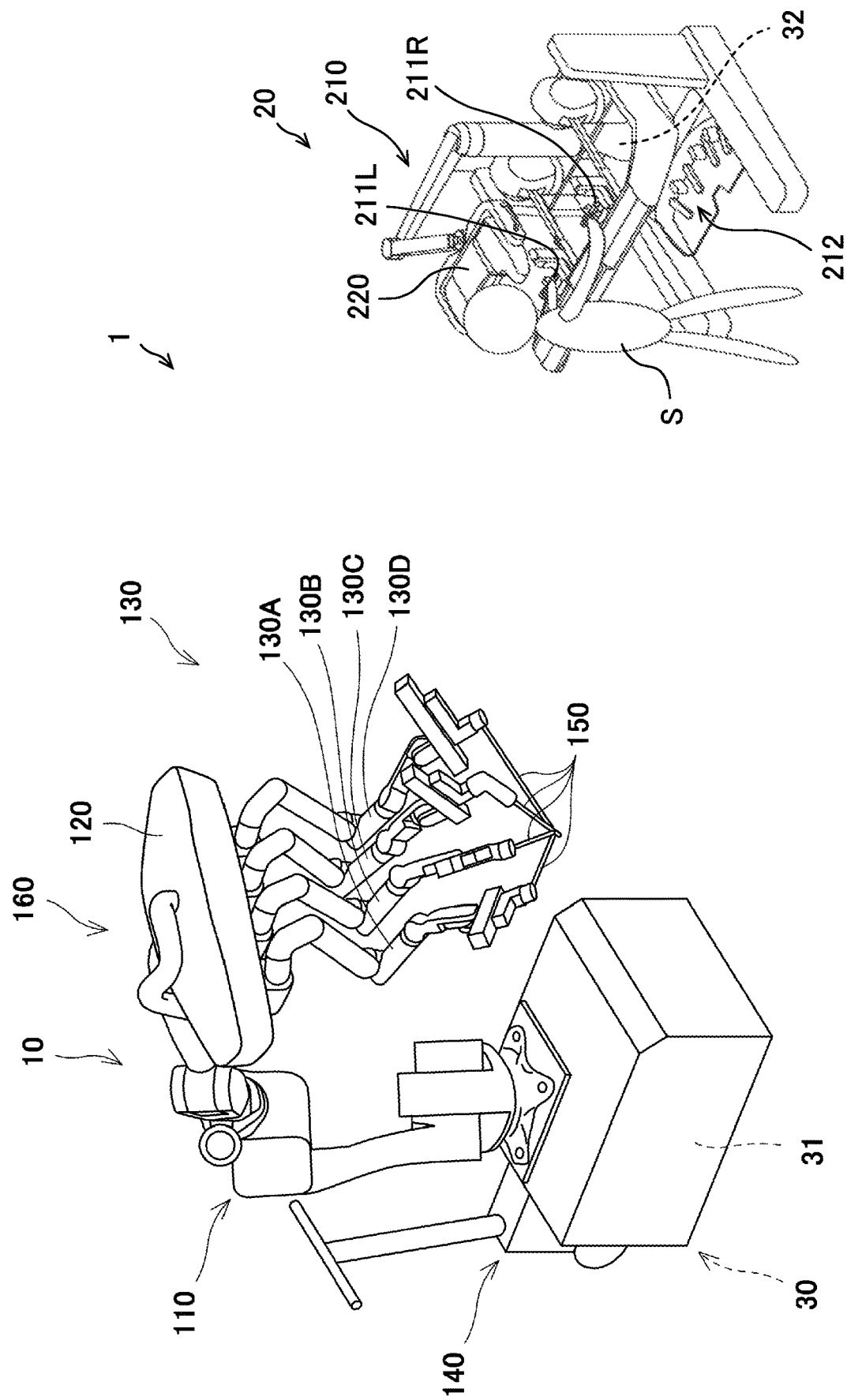
FIG. 1 is a diagram showing one example of the configuration of a surgical system according to an embodiment.

First, examples of aspects of the present disclosure will be described. A surgical robot according to one aspect of the present disclosure includes: robot arms each having plural degrees of freedom; an elongated arm base that holds base end portions of the robot arms; and a control device that controls movements of the robot arms. Each of the robot arms includes a base portion, a tip portion that holds a medical instrument, and links that couple the base portion and the tip portion and are coupled to each other. The link adjacent to the base portion is connected to the base portion through a rotational joint. At least one of the robot arms has at least seven degrees of freedom. The control device controls one robot arm having the at least seven degrees of freedom such that when viewed from a direction parallel to an axial direction of a rotation axis of the rotational joint, a first portion of a first link that is one of the links is located between a second portion of the base portion and a third portion of the tip portion.

According to the above aspect, when realizing a target position and target posture of the tip portion of the robot arm having at least seven degrees of freedom in a three-dimensional space, the robot arm has at least one additional degree of freedom. To be specific, the robot arm has a redundant degree of freedom. For example, there is a possibility that when the robot arm is operated so as to be bent, the first portion of the first link projects outward. However, the robot arm having the redundant degree of freedom operates such that the first portion is located in a region between the second portion and the third portion. Thus, the projecting of the first portion can be suppressed. Therefore, the robot arm can be prevented from contacting peripheral objects, such as the adjacent robot arm, during operation.

In the surgical robot according to one aspect of the present disclosure, the first link may have a bent shape, and the first portion may be a bent portion of the first link. According to the above aspect, for example, there is a possibility that when the robot arm is operated so as to be bent, the bent portion of the first link projects outward. However, the operation of the robot arm is controlled such that the position of the bent portion is located between the second portion and the third portion. With this, the contact between the robot arm and the peripheral object can be effectively suppressed.

In the surgical robot according to one aspect of the present disclosure, the first link may be connected to the base portion through one or more of the links, and the first link may be connected to the tip portion through one or more of the links. According to the above aspect, the robot arm has two or more degrees of freedom between the first link and the base portion and also has two or more degrees of freedom between the first link and the tip portion. For example, there is a possibility that when the robot arm is operated so as to be bent, the first link or its periphery projects outward. However, the operation of the robot arm is controlled such that the first portion of the first link is located between the second portion and the third portion. With this, the contact between the robot arm and the peripheral object can be effectively suppressed. Moreover, the operation of the robot arm can use a region around a center of the movable range of each joint connecting the links. With this, an amount where the joint can further move and a range where the robot arm can further take a posture can be increased.

In the surgical robot according to one aspect of the present disclosure, the first link may be connected to the base portion through two or more of the links, and the first link may be connected to the tip portion through two or more of the links. According to the above aspect, the number of degrees of freedom between the first link and the base portion in the robot arm and the number of degrees of freedom between the first link and the tip portion in the robot arm can be increased.

In the surgical robot according to one aspect of the present disclosure, the control device may control the one robot arm such that the first portion is located between a first plane and a second plane, the first plane passing through the second portion and extending in a direction intersecting with a longitudinal direction of the arm base, the second plane passing through the third portion and extending in the direction intersecting with the longitudinal direction. According to the above aspect, for example, when one robot arm is operated so as to be bent, the first portion of the first link is prevented from moving beyond the first plane or the second plane and projecting toward the adjacent robot arm. Therefore, the adjacent robot arms can be effectively prevented from contacting each other. The first plane and the second plane may be parallel to each other, or may not be parallel to each other. For example, the first plane and the second plane may be perpendicular to the longitudinal direction.

In the surgical robot according to one aspect of the present disclosure, the first plane may pass through the second portion and extend in a direction perpendicular to the longitudinal direction, and the second plane may pass through the third portion and extend in the direction perpendicular to the longitudinal direction. According to the above aspect, the first plane, the second plane, and a region between the first plane and the second plane can be easily set based on the arm base. With this, the control of the operation of the robot arm such that the first portion of the robot arm is located between the first plane and the second plane is facilitated.

In the surgical robot according to one aspect of the present disclosure, the control device may control the one robot arm such that the first portion is located at an intermediate position between the first plane and the second plane. According to the above aspect, the operation of the robot arm can use a region around the center of the movable range of each joint connecting the links. With this, the amount where the joint can further move and the range where the robot arm can further take a posture can be increased. The control device may control one robot arm such that the first portion is located on a plane passing through an intermediate position between the first plane and the second plane.

In the surgical robot according to one aspect of the present disclosure, the control device may control the one robot arm such that the first portion is located between the second portion and a curved surface having a reference point at the second portion and passing through the third portion. According the above aspect, for example, when one robot arm is operated so as to be bent, the first portion of the first link is prevented from projecting outward beyond the curved surface. Therefore, the contact between the robot arm and the peripheral object can be effectively suppressed. For example, the curved surface may be a sphere like surface whose center is the reference point or an axially symmetrical curved surface whose center is an axis passing through the reference point.

In the surgical robot according to one aspect of the present disclosure, the control device may control the one robot arm such that the first portion is located at an intermediate position between the second portion and the curved surface. According to the above aspect, the operation of the robot arm can use a region around the center of the movable range of each joint connecting the links. With this, the amount where the joint can further move and the range where the robot arm can further take a posture can be increased. The control device may control one robot arm such that the first portion is located on a curved surface passing through an intermediate position between the second portion and the curved surface.

A surgical system according to one aspect of the present disclosure includes: robot arms each having plural degrees of freedom; an elongated arm base that holds base end portions of the robot arms; a manipulation device by which at least one of the robot arms is manipulated; and a control device that controls movements of the robot arms based on manipulation of the manipulation device. At least one of the robot arms has at least seven degrees of freedom. Each of the robot arms includes a base portion, a tip portion that holds a medical instrument, and links that couple the base portion and the tip portion and are coupled to each other. The link adjacent to the base portion is connected to the base portion through a rotational joint. The control device moves the robot arm based on the manipulation of the manipulation device under such an operation restriction that the medical instrument is moved while maintaining a state where the medical instrument passes through a preset remote center position. The control device controls the robot arm having the at least seven degrees of freedom and manipulated by the manipulation device such that when viewed from a direction parallel to an axial direction of a rotation axis of the rotational joint, a first portion of a first link that is one of the links is located between a second portion of the base portion and a third portion of the tip portion. According to the above aspect, the same effects as the surgical robot according to one aspect of the present disclosure can be obtained.

A control method according to one aspect of the present disclosure is a method of controlling a surgical robot including an arm base, the arm base including robot arms, the robot arms each having plural degrees of freedom and including: a base portion; a tip portion that holds a medical instrument; and links that couple the base portion and the tip portion and are coupled to each other. At least one of the robot arms has at least seven degrees of freedom. The link adjacent to the base portion is connected to the base portion through a rotational joint. The method includes moving one robot arm having the at least seven degrees of freedom such that when viewed from a direction parallel to an axial direction of a rotation axis of the rotational joint, a first portion of a first link that is one of the links is located between a second portion of the base portion and a third portion of the tip portion. According to the above aspect, the same effects as the surgical robot according to one aspect of the present disclosure can be obtained.

In the control method according to one aspect of the present disclosure, the first link may have a bent shape, and the first portion may be a bent portion of the first link.

In the control method according to one aspect of the present disclosure, the first link may be connected to the base portion through one or more of the links, and the first link may be connected to the tip portion through one or more of the links.

In the control method according to one aspect of the present disclosure, the first link may be connected to the base portion through two or more of the links, and the first link may be connected to the tip portion through two or more of the links.

In the control method according to one aspect of the present disclosure, the one robot arm may be operated such that the first portion is located between a first plane and a second plane, the first plane passing through the second portion and extending in a direction intersecting with a longitudinal direction of the arm base, the second plane passing through the third portion and extending in the direction intersecting with the longitudinal direction.

In the control method according to one aspect of the present disclosure, the first plane may pass through the second portion and extend in a direction perpendicular to the longitudinal direction, and the second plane may pass through the third portion and extend in the direction perpendicular to the longitudinal direction.

In the control method according to one aspect of the present disclosure, the one robot arm may be moved such that the first portion is located at an intermediate position between the first plane and the second plane.

In the control method according to one aspect of the present disclosure, the one robot arm may be moved such that the first portion is located between the second portion and a curved surface having a reference point at the second portion and passing through the third portion.

In the control method according to one aspect of the present disclosure, the one robot arm may be moved such that the first portion is located at an intermediate position between the second portion and the curved surface.

Embodiments

Hereinafter, embodiments of the present disclosure will be described with reference to the drawings. The embodiments described below are comprehensive or specific examples. Among components in the following embodiments, components that are not recited in independent claims which embody the broadest concept of the present disclosure will be described as optional components. The diagrams in the attached drawings are schematic diagrams and are not necessarily strictly drawn. In the diagrams, the same reference signs are used for the substantially identical components, and the repetition of the same explanation may be avoided, or such explanation may be simplified. Moreover, in the present description and the claims, a "device" may denote not only a single device but also a system including devices.

Configuration of Surgical System

The configuration of a surgical system 1 according to the embodiment will be described. FIG. 1 is a diagram showing one example of the configuration of the surgical system 1 according to the embodiment. As shown in FIG. 1, the surgical system 1 includes a robot 10, a console 20, and a control device 30. The control device 30 includes a first control device 31 and a second control device 32. In the present embodiment, the surgical system 1 is a system in which a surgeon S, such as a doctor, uses the robot 10 to perform surgery, such as endoscopic surgery, for a patient as robot assisted surgery, robot remote surgery, or the like. The robot 10 and the first control device 31 constitute a surgical robot.

In the present embodiment, the surgical system 1 is a system utilizing the robot 10 that is of a master-slave type. The console 20 constitutes a master machine, and the robot 10 constitutes a slave machine. The console 20 is arranged away from the robot 10, and the robot 10 is subjected to remote manipulation by the console 20 during surgery. The surgical system 1 can perform surgery in such a manner that: the surgeon S manipulates and operates a manipulation input device 210 of the console 20 to input a command to the manipulation input device 210; and the robot 10 performs an operation corresponding to the command. The manipulation input device 210 is one example of a manipulation device.

Configuration of Robot

One example of the configuration of the robot 10 will be described. As shown in FIG. 1, the robot 10 constitutes an interface between the surgical system 1 and the patient. For example, the robot 10 is arranged beside an operating table on which the patient lies in an operating room. The robot 10 includes a positioner 110, an arm base 120, arms 130, a base 140, and the first control device 31.

The positioner 110 extends from the base 140 and couples the base 140 and the arm base 120. The positioner 110 is constituted as a robot arm. In the present embodiment, the positioner 110 is constituted as a vertical articulated robot arm. The positioner 110 can freely move the position and posture of the arm base 120 relative to the base 140 in a three-dimensional space. The configuration of the positioner 110 is not especially limited as long as the positioner 110 supports the arm base 120. For example, the positioner 110 may include a linear motion device, a lifting device, a fixing device, and the like. The fixing device may be, for example, a bracket by which the arm base 120 is fixed to a ceiling, a wall, or the like. The configuration of the base 140 is not especially limited as long as the base 140 can support the positioner 110. In the present embodiment, the base 140 is constituted as a movable cart.

The arms 130 are also called manipulator arms and are detachably attached to and supported by the arm base 120 having an elongated shape. In the present embodiment, four arms 130A to 130D are arranged at the arm base 120 so as to be lined up in a first direction. In the present embodiment, the first direction is a direction in which the arm base 120 extends and is also a longitudinal direction of the arm base 120. That the arms 130A to 130D are arranged so as to be lined up in the first direction may denote that base end portions of the arms 130A to 130D are arranged so as to be lined up in the first direction. In this case, the base end portions of the arms 130A to 130D may be arranged along the first direction as a whole. For example, that the base end portions of the arms 130A to 130D are arranged so as to be lined up in the first direction may denote that the base end portions of the arms 130A to 130D are arranged so as to be aligned along a line extending in the first direction or that at least a few of the base end portions deviate from the line. Moreover, the number of arms 130 arranged at the arm base 120 may be any number, and the arrangement of the arms 130 may be any arrangement. In the following, the wording "arms 130A to 130D" is used when these four arms are distinguished from each other, and the wording "arms 130" is used when these four arms are not distinguished from each other.

The arms 130 are constituted as robot arms. In the present embodiment, the arms 130 are constituted as vertical articulated robot arms. Each of the arms 130 can freely move the position and posture of a tip portion of the arm 130 relative to the arm base 120 in a three-dimensional space.

Each of the tip portions of the arms 130 is constituted as an instrument holding portion that can hold a surgical instrument 150 that is one example of a medical instrument. For example, the tip portion of one of the arms 130 holds an endoscope camera as the surgical instrument 150, and the tip portion of another arm 130 holds an instrument, such as a surgery instrument, as the surgical instrument 150. The surgery instrument denotes an actual operated portion which is inserted into a surgical portion of an abdominal cavity of the patient and can be driven from an outside of the abdominal cavity to execute a desired treatment or a medical function with respect to a target tissue of the surgical portion. For example, the surgery instrument includes a pair of jaws. The surgery instrument may be a surgical instrument, such as forceps, a grasper, scissors, a stapler, a needle holder, or an electric scalpel. The surgery instrument may be an electrically driven instrument, such as an electrosurgical electrode, a transducer, or a sensor. The surgery instrument may be a nozzle supplying a fluid for suctioning, injecting gas, washing, a treatment fluid, introducing an accessory, removing biopsy tissue, or the like. For example, the endoscope camera may include objective lens and a light guide.

In the robot 10, the arm base 120 serves as a "hub" for the arms 130. The positioner 110 and the arm base 120 constitute a manipulator supporting body 160 that supports the arms 130 such that the arms 130 are movable.

In the robot 10 described as above, components from the positioner 110 to the surgical instrument 150 are coupled to each other in series. In the present description and the claims, regarding each of these components, an end portion located closer to a portion where the positioner 110 and the base 140 are connected to each other may be referred to as a "base end portion," and an opposite end portion may be referred to as a "tip portion."

Figure 2:
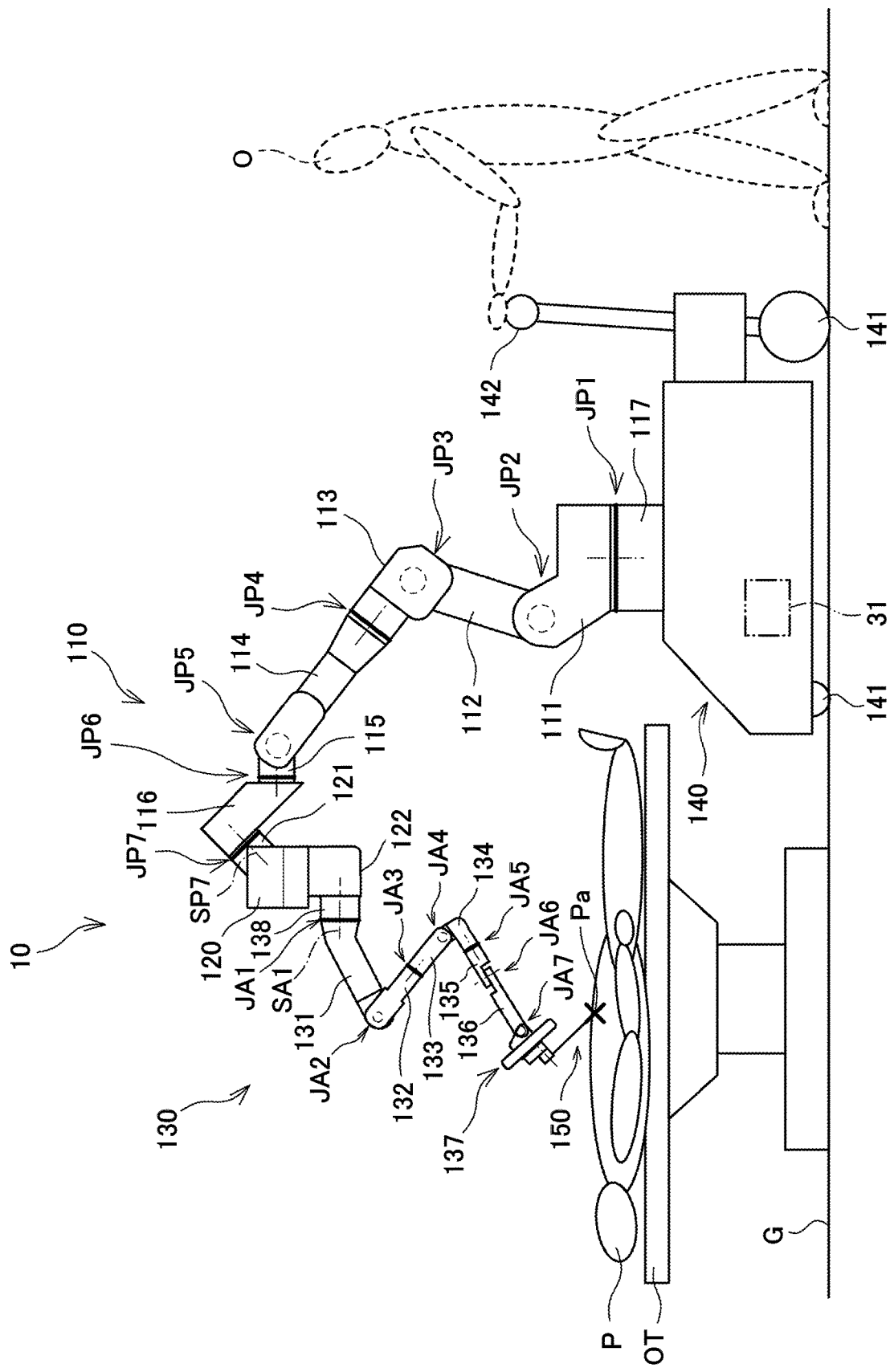
FIG. 2 is a side view showing one example of the configuration of a robot according to the embodiment.

FIG. 2 is a side view showing one example of the configuration of the robot 10 according to the embodiment. As shown in FIG. 2, the base 140 includes wheels 141 and a handle 142. The handle 142 can turn together with the wheels 141. The surgeon S or a surgical assistant O can hold the handle 142 and push or pull the handle 142 to move the base 140 and can turn the handle 142 to change a proceeding direction of the base 140.

The positioner 110 includes positioner links 111 to 116 and a base portion 117. The base portion 117 is detachably attached to an upper portion of the base 140. The positioner links 111 to 116 are sequentially coupled to each other and extend from the base portion 117.

The base end portion of the positioner link 111 is coupled to the base portion 117 through a rotary joint JP1 so as to be turnable about an axis extending in a vertical direction. The vertical direction is a direction perpendicular to a floor surface G on which the base 140 is arranged, and a horizontal direction is a direction parallel to the floor surface G. The base end portion of the positioner link 112 is coupled to the tip portion of the positioner link 111 through a rotary joint JP2 so as to be rotatable about an axis extending in the horizontal direction. The base end portion of the positioner link 113 is coupled to the tip portion of the positioner link 112 through a rotary joint JP3 so as to be rotatable about an axis extending in the horizontal direction. The base end portion of the positioner link 114 is coupled to the tip portion of the positioner link 113 through a rotary joint JP4 so as to be twistingly rotatable. For example, a twist rotation axis may be an axis extending in a direction along a central axis where the tip portion of the positioner link 113 extends. The base end portion of the positioner link 115 is coupled to the tip portion of the positioner link 114 through a rotary joint JP5 so as to be rotatable about an axis extending in a direction perpendicular to a direction along a central axis where the tip portion of the positioner link 114 extends. The base end portion of the positioner link 116 is coupled to the tip portion of the positioner link 115 through a rotary joint JP6 so as to be twistingly rotatable. A first attaching portion 121 of the arm base 120 is coupled to the tip portion of the positioner link 116 through a rotary joint JP7 so as to be twistingly rotatable.

The positioner 110 configured as above is constituted as a multiaxial joint arm having plural degrees of freedom, specifically as a seven-axis joint arm having seven degrees of freedom.

The arm base 120 includes one first attaching portion 121 and plural second attaching portions 122. The first attaching portion 121 is arranged at an upper portion of the arm base 120 and constitutes a mechanical interface connected to the positioner link 116. The second attaching portions 122 are arranged at a lower portion of the arm base 120 and constitute mechanical interfaces connected to the base end portions of the arms 130. In the present embodiment, four second attaching portions 122 are arranged. The arm base 120 is twistingly rotatable relative to the positioner link 115 about a twist rotation axis SP7 of the rotary joint JP7.

Figure 3:
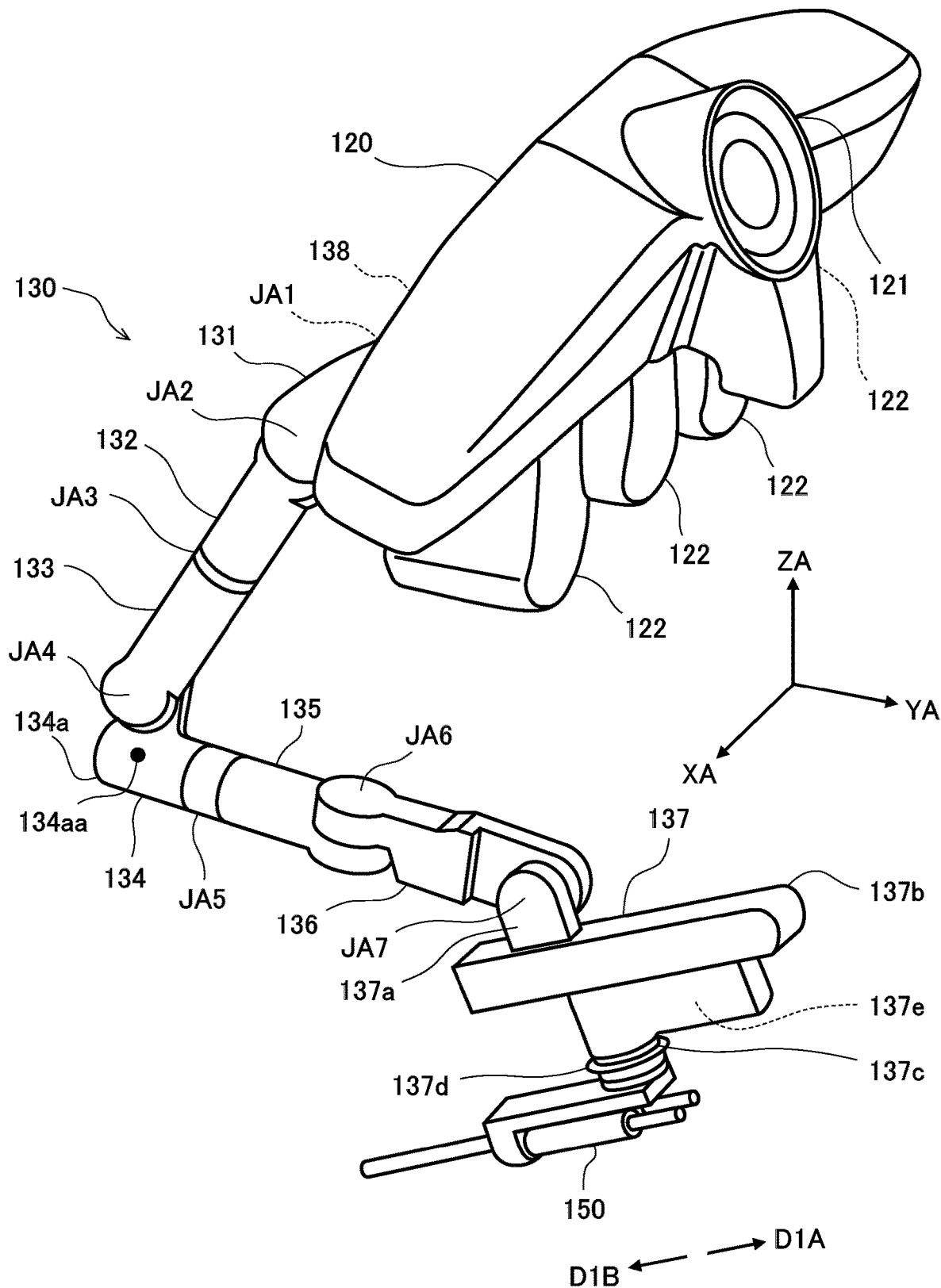
FIG. 3 is a perspective view showing one example of the configuration of an arm of the robot according to the embodiment.
Figure 4:
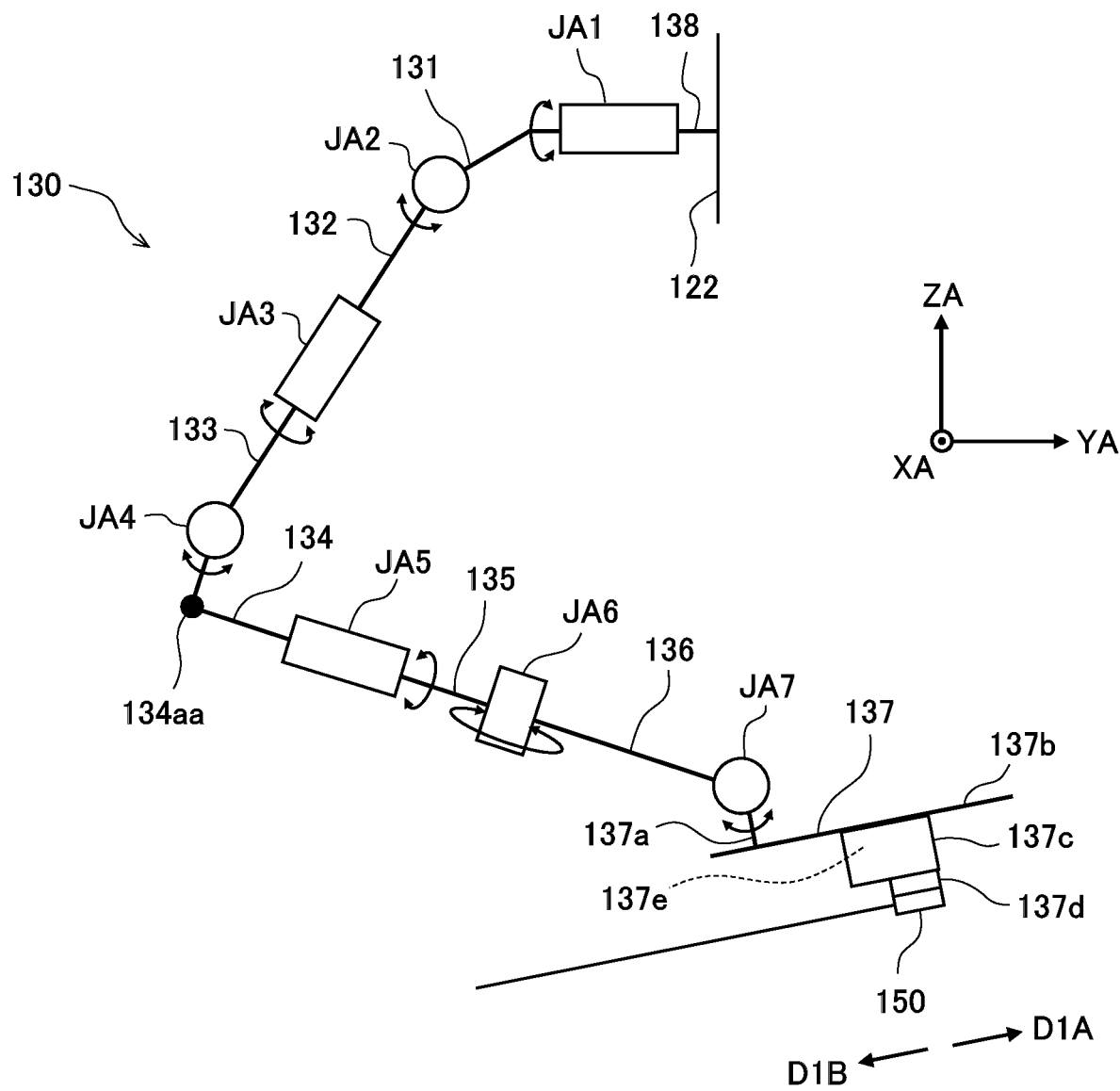
FIG. 4 is a diagram showing a model of the arm of FIG. 3.

FIG. 3 is a perspective view showing one example of the configuration of the arm 130 of the robot 10 according to the embodiment. FIG. 4 is a diagram showing a model of the arm 130 of FIG. 3. Each of FIG. 3 and FIG. 4 shows one arm 130. Each of the other three arms 130 is the same in configuration as the illustrated arm 130. As shown in FIG. 2 to FIG. 4, the arm 130 includes links 131 to 136, a tip link 137, and a base link 138. The base link 138 is detachably attached to the second attaching portion 122 of the arm base 120. The links 131 to 136 are sequentially coupled to each other and extend from the base link 138. The tip link 137 is coupled to the link 136. The base link 138 is one example of a base portion of a robot arm, and the tip link 137 is one example of a tip portion of a robot arm.

The base end portion of the link 131 is coupled to the base link 138 through a rotary joint JA1 so as to be twistingly rotatable. The link 131 has such a bent shape that a direction along a central axis where the tip portion of the link 131 extends is obliquely inclined relative to a direction along a central axis where the base end portion of the link 131 extends. However, the link 131 is not limited to this. For example, an angle formed by the direction along the central axis where the base end portion of the link 131 extends and the direction along the central axis where the tip portion of the link 131 extends may be 90 degrees or more and 180 degrees or less, specifically 140 degrees. The rotary joint JA1 constitutes a twisting joint.

The base end portion of the link 132 is coupled to the tip portion of the link 131 through a rotary joint JA2 so as to be rotatable about an axis extending in a direction perpendicular to the direction along the central axis where the tip portion of the link 131 extends. The link 132 is a linear link. The rotary joint JA2 constitutes a bending joint.

The base end portion of the link 133 is coupled to the tip portion of the link 132 through a rotary joint JA3 so as to be twistingly rotatable. The link 133 is a linear link. The rotary joint JA3 constitutes a twisting joint.

The base end portion of the link 134 is coupled to the tip portion of the link 133 through a rotary joint JA4 so as to be rotatable about an axis extending in a direction perpendicular to a direction along a central axis where the tip portion of the link 133 extends. The link 134 has a shape which is bent in such an L shape that a direction along a central axis where the tip portion of the link 134 extends is perpendicular to a direction along a central axis where the base end portion of the link 134 extends. A bent portion 134a of the link 134 corresponds to an elbow of the arm 130. The link 134 may be bent such that the direction along the central axis where the tip portion of the link 134 extends is obliquely inclined relative to the direction along the central axis where the base end portion of the link 134 extends. For example, an angle formed by the direction along the central axis where the base end portion of the link 134 extends and the direction along the central axis where the tip portion of the link 134 extends may be 70 degrees or more and 110 degrees or less. The rotary joint JA4 constitutes a bending joint.

The base end portion of the link 135 is coupled to the tip portion of the link 134 through a rotary joint JA5 so as to be twistingly rotatable. The link 135 is a linear link. The rotary joint JA5 constitutes a twisting joint.

The base end portion of the link 136 is coupled to the tip portion of the link 135 through a rotary joint JA6 so as to be rotatable about an axis extending in a direction perpendicular to a direction along a central axis where the tip portion of the link 135 extends. The link 136 is a linear link. The rotary joint JA6 constitutes a bending joint.

The base end portion of the tip link 137 is coupled to the tip portion of the link 136 through a rotary joint JA7 so as to be rotatable about an axis extending in a direction perpendicular to a direction along a central axis where the tip portion of the link 136 extends. A direction along a rotation axis of the rotary joint JA7 is a direction intersecting with a direction along a rotation axis of the rotary joint JA6, specifically a direction perpendicular to the direction along the rotation axis of the rotary joint JA6. The rotary joint JA6 constitutes a bending joint.

The arm 130 described as above is constituted as a multiaxial joint arm having plural degrees of freedom, specifically as a seven-axis joint arm having seven degrees of freedom. The arm 130 as the seven-axis joint arm has six degrees of freedom necessary to realize a target position and target posture of the tip link 137 in a three-dimensional space, and one additional degree of freedom, i.e., a redundant degree of freedom. According to such arm 130, even when the position and posture of the tip link 137 relative to the base link 138 are specified, the positions and postures of the links 131 to 136 are not uniquely determined.

Moreover, the tip link 137 includes a first coupling portion 137a, a translational unit 137b, a second coupling portion 137c, and a holder 137d. The first coupling portion 137a couples the rotary joint JA7 and the translational unit 137b. The second coupling portion 137c couples the translational unit 137b and the holder 137d at an opposite side of the first coupling portion 137a across the translational unit 137b. The translational unit 137b is constituted as a double speed mechanism that can move at least one of the coupling portions 137a and 137c in a direction D1A or D1B along a longitudinal direction of the translational unit 137b to change relative positions of the coupling portions 137a and 137c in the directions D1A and D1B. For example, each of the directions D1A and D1B is a direction perpendicular to the direction along the rotation axis of the rotary joint JA7.

The translational unit 137b includes a driving device 137e including a driving mechanism and a driving source. The driving mechanism is a mechanism that converts and transmits driving force of the driving source to linearly move at least one of the coupling portions 137a and 137c. The configuration of a known link mechanism is applicable to the configuration of the driving mechanism. For example, the configuration of the driving mechanism may be a configuration using a belt and a pulley, a configuration including a ball screw structure, or a configuration including a gear train. For example, the driving source may include a motor that uses electric power as a power source. In the present embodiment, the driving source includes a servomotor.

The surgical instrument 150 is attachable to the holder 137d. As shown in FIG. 3 and FIG. 4, when an instrument as the surgical instrument 150 is attached to the holder 137d, an axis of the instrument extends in, for example, the direction D1B.

As shown in FIG. 3 and FIG. 4, a coordinate system based on the arm base 120 is defined. This coordinate system is constituted by an XA axis, a YA axis, a ZA axis which are orthogonal to each other. The XA axis is an axis parallel to a direction in which the base links 138 of the four arms 130 are lined up. A direction from the arm 130A toward the arm 130D in FIG. 1 is an XA axis positive direction. The YA axis is an axis parallel to a direction perpendicular to a connection surface (not shown) of the second attaching portion 122 which surface is connected to the base link 138 of the arm 130. Specifically, the second attaching portion 122 includes a hole (not shown) into which the base link 138 of the arm 130 is inserted, and a central axis SA1 (see FIG. 2) of the hole is parallel to the YA axis. The central axis SA1 is also parallel to a rotation axis of the joint JA1. A direction from the second attaching portion 122 toward the base link 138 is a YA-axis negative direction. The ZA axis is an axis perpendicular to the XA axis and the YA axis. A direction from the first attaching portion 121 toward the second attaching portion 122 in the arm base 120 is a ZA-axis negative direction.

Figure 5:
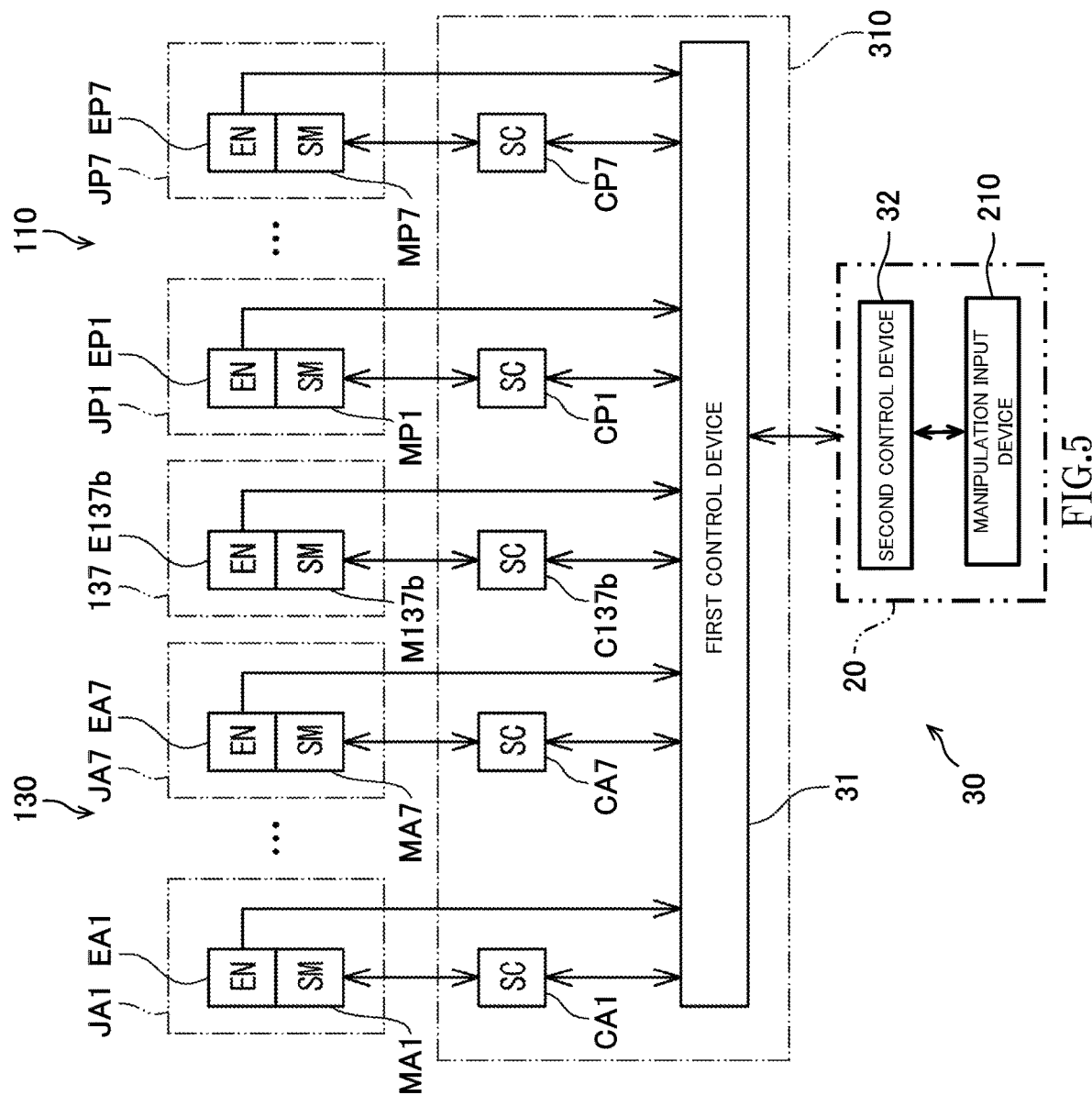
FIG. 5 is a block diagram showing one example of a control device and its peripheral components in the surgical system according to the embodiment.

FIG. 5 is a block diagram showing one example of the configuration of the control device 30 and its peripheral components in the surgical system 1 according to the embodiment. As shown in FIG. 5, in the positioner 110, each joint (JP1 to JP7) includes: a servomotor (MP1 to MP7; shown by "SM" in FIG. 5); and a rotation sensor (EP1 to EP7; shown by "EN" in FIG. 5), such as an encoder. The servomotors MP1 to MP7 are motors that respectively drive the joints JP1 to JP7 to rotate. The rotation sensors EP1 to EP7 are sensors that respectively detect rotation amounts (for example, rotation angles) of the servomotors MP1 to MP7. Motor reducers (not shown) may be provided with the servomotors MP1 to MP7, respectively.

In the arm 130, each joint (JA1 to JA7) includes a servomotor (MA1 to MA7) and a rotation sensor (EA1 to EA7). The servomotors MA1 to MA7 respectively drive the joints JA1 to JA7 to rotate. The rotation sensors EA1 to EA7 respectively detect rotation amounts of the servomotors MA1 to MA7. Motor reducers (not shown) may be provided with the servomotors MA1 to MA7, respectively.

The tip link 137 of the arm 130 includes: a servomotor M137b that drives the translational unit 137b to translate; and a rotation sensor E137b that detects a rotation amount of the servomotor M137b. A motor reducer (not shown) may be provided with the servomotor M137b.

In FIG. 5, only one arm 130 is shown, and the other arms 130 are not shown. Each of the other arms 130 is the same in configuration as the illustrated arm 130. The rotation sensor is not limited to an encoder and may be a sensor that can detect the rotation amount of the servomotor, the rotation amount of the joint, or the like.

The control device 30 includes the first control device 31 and the second control device 32. The first control device 31 of the robot 10 controls the operation of the entire robot 10, and the second control device 32 of the console 20 controls the operation of the entire console 20. For example, the first control device 31 and the second control device 32 are computers. The first control device 31 is connected to the second control device 32 so as to be communicable with the second control device 32. The first control device 31 controls the robot 10 in response to the command received by the console 20. The first control device 31 transmits information and the like to the second control device 32 such that: an endoscopic image of the endoscope camera is displayed in the console 20; the console 20 performs an operation corresponding to the operation of the robot 10; and the like.

The first control device 31 is electrically connected to the servomotors MA1 to MA7 through respective driving circuits CA1 to CA7 (shown by "SC" in FIG. 5). The first control device 31 is electrically connected to the servomotors MP1 to MP7 through respective driving circuits CP1 to CP7. The first control device 31 is electrically connected to the servomotor M137b through a driving circuit C137b. The control device 30 and the driving circuits CA1 to CA7, CP1 to CP7, and C137b constitute a control unit 310. For example, each of the driving circuits CA1 to CA7, CP1 to CP7, and C137b includes an amplifying circuit and the like and adjusts a current value of a current supplied to the servomotor connected thereto in accordance with the command of the first control device 31.

The first control device 31 includes a calculation unit including a processor, a memory, and the like. The calculation unit transmits or receives information, data, commands, and the like to or from other devices, such as the console 20. The calculation unit receives detection signals from various sensors and outputs control signals to control targets. The memory includes a storage device such as a semiconductor memory, such as a volatile memory or a non-volatile memory; a hard disk, or a SSD (Solid State Drive). For example, the memory stores programs executed by the calculation unit, various fixed data, and the like.

The functions of the calculation unit may be realized by a computer system (not shown) including: a processor, such as a CPU (Central Processing Unit); a volatile memory, such as a RAM (Random Access Memory); a non-volatile memory, such as a ROM (Read-Only Memory); and the like. Some or all of the functions of the calculation unit may be realized in such a manner that the CPU uses the RAM as a work area and executes the program stored in the ROM. Some or all of the functions of the calculation unit may be realized by the computer system, may be realized by a special hardware circuit, such as an electronic circuit or an integrated circuit, or may be realized by the combination of the computer system and the hardware circuit. The first control device 31 may execute processing by centralized control performed by a single computer or may execute the processing by distributed control performed by the cooperation of plural computers.

The first control device 31 may include, for example, a microcontroller, a MPU (Micro Processing Unit), a LSI (Large Scale Integration), a system LSI, a PLC (Programmable Logic Controller), a logic circuit, or the like. Each of the functions of the first control device 31 may be realized by a single chip, or some or all of the functions of the first control device 31 may be realized by a single chip. Moreover, each circuit may be a general circuit or a special circuit. As the LSI, a FPGA (Field Programmable Gate Array) that is programmable after the manufacture of the LSI, a reconfigurable processor that can reconfigure the connection and/or setting of circuit cells inside the LSI, an ASIC (Application Specific Integrated Circuit) in which plural circuits having functions for a specific application are integrated, or the like may be utilized.

Configuration of Console

The configuration of the console 20 will be described. As shown in FIG. 1, the console 20 is a device that constitutes an interface between the surgical system 1 and the surgeon S and is used to manipulate the robot 10. The console 20 is placed beside the operating table in the operating room, away from the operating table in the operating room, or outside the operating room.

The console 20 includes: the manipulation input device 210 that receives the input of the command from the surgeon S; a display device 220 that displays an image taken by the endoscope camera; and the second control device 32. The endoscope camera as the surgical instrument is attached to the robot 10. The manipulation input device 210 includes a pair of left and right operation manipulators 211L and 211R and manipulation pedals 212. The operation manipulators 211L and 211R are devices used to manually manipulate the robot 10.

Each of the operation manipulators 211L and 211R receives manipulation force from the surgeon S and includes an operating portion (not shown) held by the surgeon S. In the present embodiment, each of the operation manipulators 211L and 211R is an operation tool that receives, for example, movement commands of the positions and postures of the endoscope camera and the surgery instrument. The manipulation pedals 212 are operation tools that receive commands regarding the zoom of the endoscope camera, the switching of control modes, the switching of the arms 130 associated with the operation manipulators 211L and 211R, and the like. The manipulation input device 210 further includes: an operation tool that receives the input of a coelom insertion command of the surgery instrument; an operation tool that receives the input of an arm return command; and the like. These operation tools may be realized by the operation manipulators 211L and 211R or the manipulation pedals 212 or may be realized by a known additional operation tool, such as a lever, a button, a touch panel, a joystick, a motion capture, or the like. The manipulation input device 210 may include a driving mechanism (not shown) that applies reaction force against the manipulation force of the surgeon S to the operation manipulators 211L and 211R.

When manually manipulating the robot 10, the surgeon S directly moves the operating portions of the operation manipulators 211L and 211R while confirming the affected part on the endoscopic image displayed on the display device 220. Thus, the surgeon S commands to move the surgical instruments 150 of the tips of the arms 130 of the robot 10. For example, the above arms 130 of the robot 10 are associated with the operation manipulators 211L and 211R by the manipulation of the manipulation pedals 212, and the associated arms 130 operate in accordance with the manipulation of the operation manipulators 211L and 211R.

As shown in FIG. 5, the second control device 32 is connected to the first control device 31 so as to be communicable with the first control device 31. For example, the second control device 32 transmits information, data, commands, and the like received by the manipulation input device 210 to the first control device 31. Moreover, based on the information, the data, the commands, and the like from the first control device 31, the second control device 32 controls the operations performed by the operation manipulators 211L and 211R, an image display operation of the display device 220, and the like. Some or all of the functions of the second control device 32 may be realized by a computer system (not shown) including a CPU, a RAM, a ROM, and the like, may be realized by a special hardware circuit, such as an electronic circuit or an integrated circuit, or may be realized by the combination of the computer system and the hardware circuit. The second control device 32 may execute processing by centralized control performed by a single computer or may execute the processing by distributed control performed by the cooperation of plural computers. The second control device 32 and the first control device 31 may be included in a single computer.

Functional Components of First Control Device and Second Control Device

Figure 6:
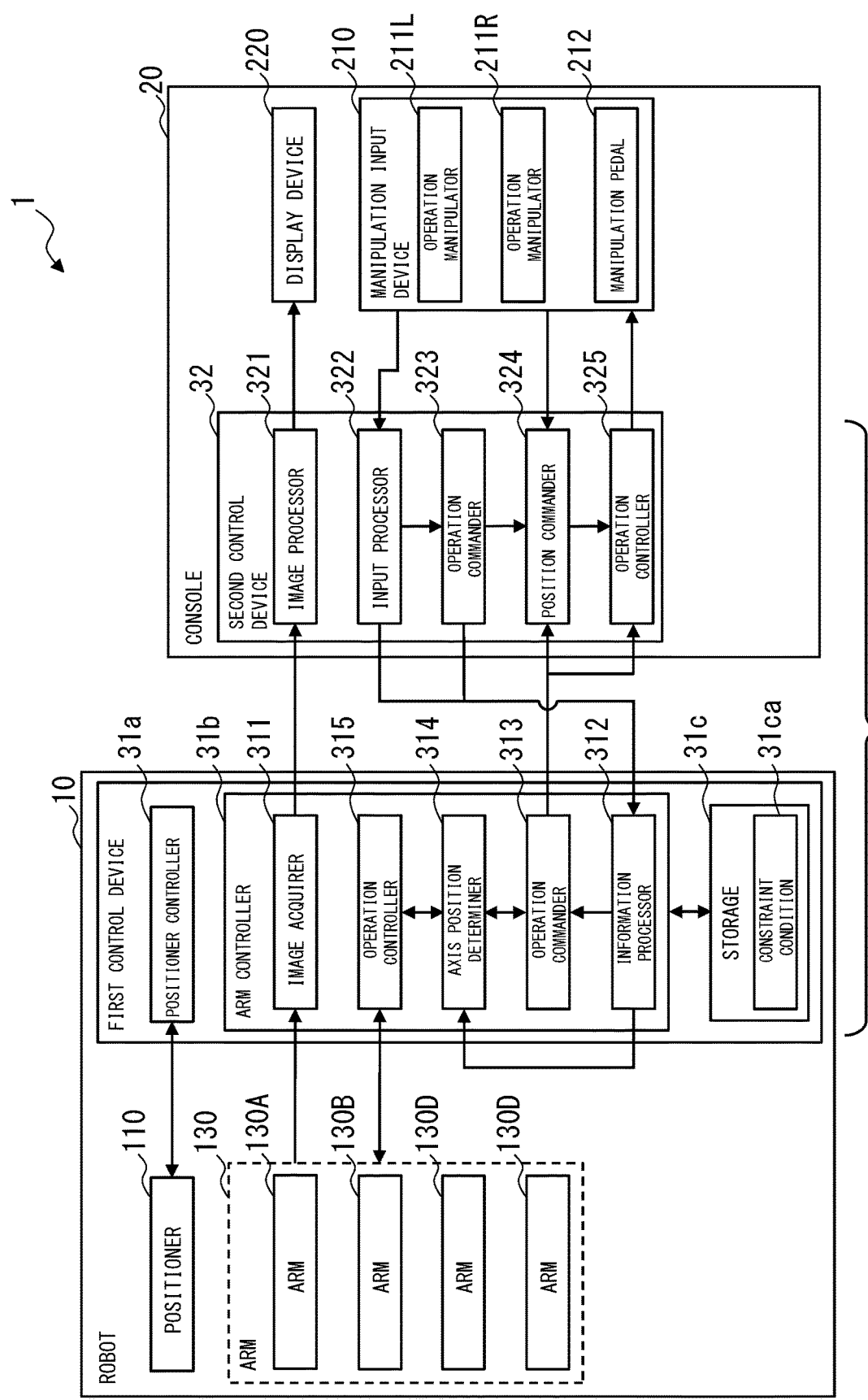
FIG. 6 is a block diagram showing one example of functional components of the control device according to the embodiment.

FIG. 6 is a block diagram showing one example of the functional components of the control device 30 according to the embodiment. As shown in FIG. 6, as the functional components, the second control device 32 of the console 20 includes an image processor 321, an input processor 322, an operation commander 323, a position commander 324, and an operation controller 325. The functions of the above functional components are realized by a processor and the like. Not all the above functional components are necessary.

The image processor 321 receives image data, taken by the endoscope camera that is one of the surgical instruments 150, from the first control device 31, outputs the image data to the display device 220, and displays the image data on the display device 220. The image processor 321 may subject the image data to conversion processing or the like and then output the image data to the display device 220.

The input processor 322 receives information, data, commands, and the like from the manipulation input device 210, processes them, and outputs them to the first control device 31 and/or the operation commander 323. For example, the input processor 322 detects rotation amounts of joints of the operation manipulators 211L and 211R from detected values of rotation sensors disposed at the joints of the operation manipulators 211L and 211R and calculates the positions and speeds (movement speeds) of the operating portions from the rotation amounts of the joints. Based on the positions and speeds of the operating portions calculated by the input processor 322, the operation commander 323 generates a movement command that commands, for example, the positions and speeds of the positioner 110 and the arms 130 of the robot 10. Force sensors that detect force applied to the operation manipulators 211L and 211R may be disposed. The input processor 322 may detect force detected values regarding the magnitude, directions, and the like of the force from the detected values of the force sensors, and the operation commander 323 may generate, based on the force detected values, a force command that commands the magnitude, direction, and the like of the force applied from the arm 130 of the robot 10 to a target object. The operation commander 323 may generate a movement command by using acceleration corresponding to the force detected values. The operation commander 323 outputs a manipulation operating command including the movement command, the force command, and the like to the first control device 31.

The position commander 324 receives a position command from the first control device 31. The position command includes position and posture commands corresponding to the positions, postures, and the like of the positioner 110 and the arm 130 of the robot 10. For example, the position command includes position and posture commands corresponding to the positions, the postures, and the like of the joints of the positioner 110, the joints of the arm 130, and the like. Based on the received position command and movement command, the position commander 324 generates a manipulation position command that commands the positions, postures, and the like of the operating portions of the operation manipulators 211L and 211R such that the positions and postures of the operating portions of the operation manipulators 211L and 211R correspond to the tip links 137 of the arms 130 of the robot 10. The content of the manipulation position command may include force applied to the operating portions of the operation manipulators 211L and 211R. Moreover, the position commander 324 detects the positions of the joints of the operation manipulators 211L and 211R from the detected values of the rotation sensors disposed at the joints. The operation controller 325 performs control of supplying current to the servomotors of the corresponding joints based on the manipulation position command. As a result, the positions and postures of the operating portions of the operation manipulators 211L and 211R move so as to correspond to the positions and postures of the arms 130 and the surgical instruments 150.

The first control device 31 includes a positioner controller 31a, an arm controller 31b, and a storage 31c as the functional components. The positioner controller 31a controls the operation of the positioner 110, and the arm controller 31b controls the operations of the arms 130 and the surgical instruments 150. The functions of the positioner controller 31a and the arm controller 31b are realized by a processor and the like, and the function of the storage 31c is realized by a memory.

Based on a command regarding, for example, the setting of preparation positions input to an input device (not shown) disposed at the robot 10, the positioner controller 31a performs control of moving the positioner 110, the arm base 120, and the arms 130 to the preparation positions stored in the storage 31c.

For example, as shown in FIG. 2, at the time of the surgery, the surgical assistant O (or the surgeon) moves the robot 10 close to an operating table OT by using the base 140. At this time, the positioner 110, the arm base 120, and the arms 130 are located at predetermined retracting positions (not shown) that are set relative to the base 140. After the robot 10 is moved, the surgical assistant O inputs, to the input device (not shown) of the robot 10, selection of the preparation positions corresponding to the details of the surgery of a patient P. With this, the positioner controller 31a reads the corresponding information of the preparation positions from the storage 31c and moves the positioner 110 and the like such that the positioner 110, the arm base 120, and the arms 130 are located at the preparation positions. The positions of the positioner 110, the arm base 120, and the arms 130 can be individually adjusted from the preparation positions by using the input device of the robot 10.

In the present embodiment, while the positioner 110, the arm base 120, and the arms 130 move from the retracting positions to the preparation positions, the first control device 31 does not receive the manipulation performed by the manipulation input device 210. After the completion of the positioning at the preparation positions, the first control device 31 can receive the manipulation performed by the manipulation input device 210. During the surgery performed after the completion of the positioning at the preparation positions, the first control device 31 performs such operation control that, as a general rule, in a state where the positioner 110 and the arm base 120 remain stationary, each arm 130 is operated in accordance with the command from the manipulation input device 210 to suitably change the position and posture of the surgical instrument 150.

The arm controller 31b includes an image acquirer 311, an information processor 312, an operation commander 313, an axis position determiner 314, and an operation controller 315 as the functional components. Not all the functional components are necessary.

The storage 31c can store, i.e., memorize various information, and allow the stored information to be read out. For example, the storage 31c stores the information of the preparation positions of the positioner 110, the arm base 120, and the arms 130. The storage 31c stores a remote center position for the surgery. The storage 31c stores a constraint condition 31ca used in a restriction mode. The storage 31c may store the information of the surgical instrument 150 that is attached to the tip link 137 of each arm 130. The information of the surgical instrument 150 may include information of the type, shape, dimension, operating direction, operating range, and the like of the surgical instrument 150. The storage 31c may store programs that realize the functions of the first control device 31.

The remote center position is a reference position of the posture of the surgical instrument 150, such as the posture of the instrument, during the surgery. For example, the first control device 31 may perform control of operating the arm 130 while maintaining a state where the instrument as the surgical instrument 150 passes through the remote center position during the surgery. For example, that the instrument passes through the remote center position denotes that the instrument passes through the remote center position, that an extended line of a center line, such as a central axis, of the instrument passes through the remote center position, and the like. At this time, the first control device 31 bends and moves the arm 130 to variously change the posture and insertion depth of the instrument based on the remote center position. To be specific, the first control device 31 controls the movement of the arm 130 with operation restriction. One example of the remote center position is a position Pa on the patient P shown in FIG. 2. For example, the position Pa may be taught in a process in which the surgical assistant O prepares for the surgery, and may be stored in the storage 31c.

The constraint condition 31ca may be a condition that restricts the operating range of each arm 130. Specifically, the constraint condition 31ca includes the position of a restriction portion set at the arm 130 and a restriction range that is a range in which the restriction portion can be located when the arm 130 operates, such that the position of the restriction portion and the restriction range are associated with each other. The constraint condition 31ca is a condition regarding the operation of each arm 130 relative to the arm base 120 and is based on the arm base 120.

The position of the restriction portion may be set at any position of the arm 130. In the present embodiment, the position of the restriction portion is set at the bent portion 134a of the link 134. Specifically, the position of the restriction portion is set at a bending point 134aa (see FIG. 3 and FIG. 4) of a central axis where the bent portion 134a of the link 134 extends. The link 134 is one example of a first link, and the bending point 134aa is one example of a first portion.

For example, as shown in FIG. 2, the robot 10 bends and operates the arm 130 to variously change the posture and insertion depth of the surgical instrument 150 relative to a remote center point Pa that is a remote center point of the rotation of the posture of the surgical instrument 150 and is located at the surgical portion of the patient P who lies on the operating table OT. At this time, the arm 130 bends at the link 134 located in the vicinity of an intermediate position between the tip link 137 and the base link 138. Especially, there is a possibility that when the arm 130 bends at the link 134 at an acute angle, the bent portion 134a (see FIG. 3) of the link 134 largely projects to an upper side and/or a lateral side and contacts the adjacent arm 130. Therefore, in the present embodiment, the bending point 134aa of the bent portion 134a of the link 134 is set as the restriction portion.

The restriction range of each arm 130 is not a range determined based on a positional relation among the arm 130 and the other arms 130 but a range determined based on the state of the arm 130. The restriction range is not a range fixed to the arm 130 but a range that changes in accordance with the state of the arm 130.

Specifically, the restriction range is a region between a portion of the base link 138 located at a specific position of the base link 138 and a portion of the tip link 137 located at a specific position of the tip link 137. For example, the above region may be a region when viewed from a direction parallel to an axial direction of a rotation axis of the rotary joint JA1.

Figure 7:
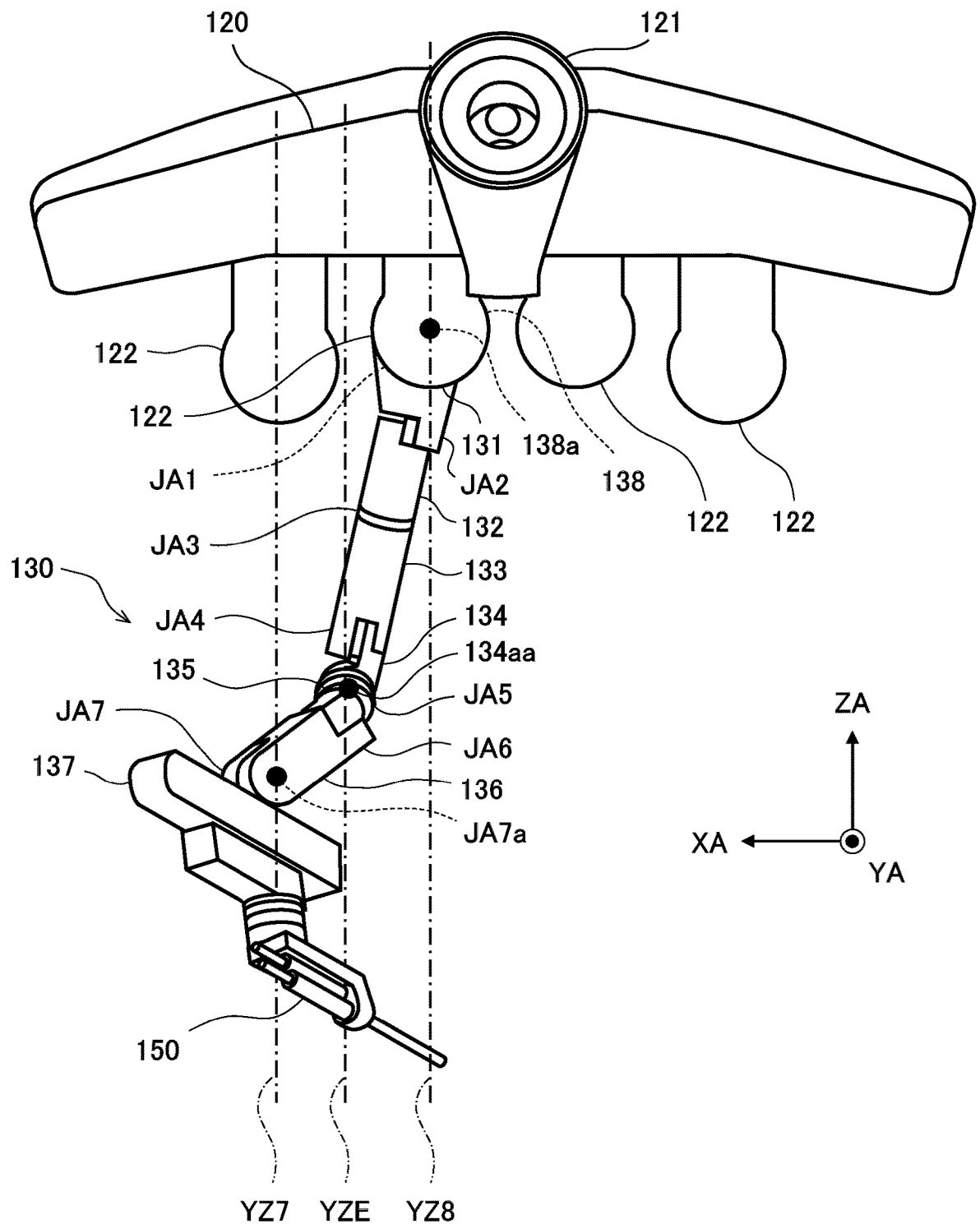
FIG. 7 is a side view of the arm of FIG. 3 when viewed in a YA-axis negative direction.
Figure 8:
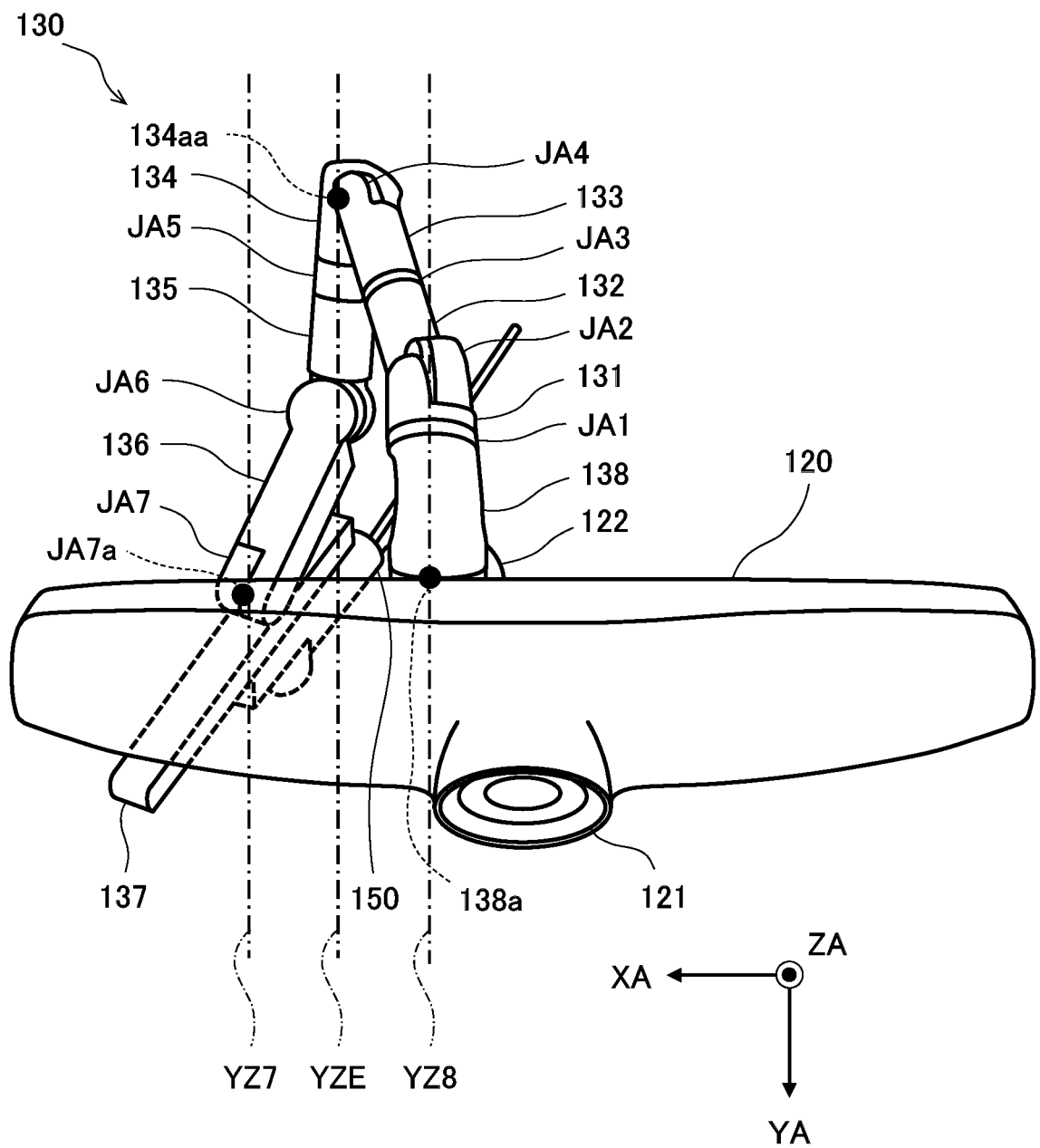
FIG. 8 is a plan view of the arm of FIG. 3 when viewed in a ZA-axis negative direction.

FIG. 7 is a side view of the arm 130 of FIG. 3 when viewed from the YA-axis negative direction, and FIG. 8 is a plan view of the arm 130 of FIG. 3 when viewed from the ZA-axis negative direction. As shown in FIG. 7 and FIG. 8, the portion located at the specific position in the base link 138 is set at a point 138a, and the portion located at the specific position in the tip link 137 is set at a point JA7a. The point 138a is an intersection point where a connection surface between the base link 138 and the second attaching portion 122 intersects with a central axis where the base link 138 extends. The point JA7a is located at a connection portion between the tip link 137 and the link 136. Specifically, the point JA7a is a center point of the connection portion in the axial direction of the rotation axis of the rotary joint JA7 which intersects with the first coupling portion 137a. The restriction range may be, for example, an intermediate position between the point 138a and the point JA7a. In the present description and the claims, the "intermediate position" may denote a middle position between two elements and a position in the vicinity of the middle position. The base link 138 is one example of a second link, and the point 138a is one example of a second portion. The tip link 137 is one example of a third link, and the point JA7a is one example of a third portion.

Moreover, the restriction range may be a three-dimensional region between a first plane that passes through the point 138a and extends in a direction intersecting with the XA axis and a second plane that passes through the point JA7a and extends in the direction intersecting with the XA axis. The first plane and the second plane may be parallel to each other or may not be parallel to each other. The axial direction of the XA axis is one example of the longitudinal direction of the arm base 120.

For example, as shown in FIG. 7 and FIG. 8, the first plane may be a plane YZ8 perpendicular to the XA axis, and the second plane may be a plane YZ7 perpendicular to the XA axis. The plane YZ7 passes through the point JA7a and is parallel to a YAZA plane. The plane YZ8 passes through the point 138a and is parallel to the YAZA plane. Therefore, the restriction range may be a three-dimensional region between the first plane that passes through the point 138a and extends in a direction perpendicular to the XA axis and the second plane that passes through the point JA7a and extends in the direction perpendicular to the XA axis. In the present description and the claims, the terms "perpendicular," "vertical," "horizontal," and "parallel" may respectively denote "completely perpendicular," "completely vertical," "completely horizontal," and "completely parallel" and also may respectively denote "substantially perpendicular," "substantially vertical," "substantially horizontal," and "substantially parallel" which may be respectively near "completely perpendicular," "completely vertical," "completely horizontal," and "completely parallel".

The restriction range may be an intermediate position between the first plane and the second plane. For example, the restriction range may be an intermediate position between the plane YZ7 and the plane YZ8.

Moreover, the restriction range may be a two-dimensional region on a third plane between the first plane and the second plane. The third plane may be parallel to at least either one of the first plane or the second plane or may not be parallel to the first plane and the second plane. The third plane may be located at an intermediate position between the first plane and the second plane. For example, as shown in FIG. 7 and FIG. 8, the third plane may be a plane YZE between the plane YZ7 and the plane YZ8. The plane YZE is parallel to the planes YZ7 and YZ8 but may not be parallel to the planes YZ7 and YZ8. The position of the plane YZE may be between the plane YZ7 and the plane YZ8. For example, the position of the plane YZE may be an intermediate position between the plane YZ7 and the plane YZ8.

Figure 9:
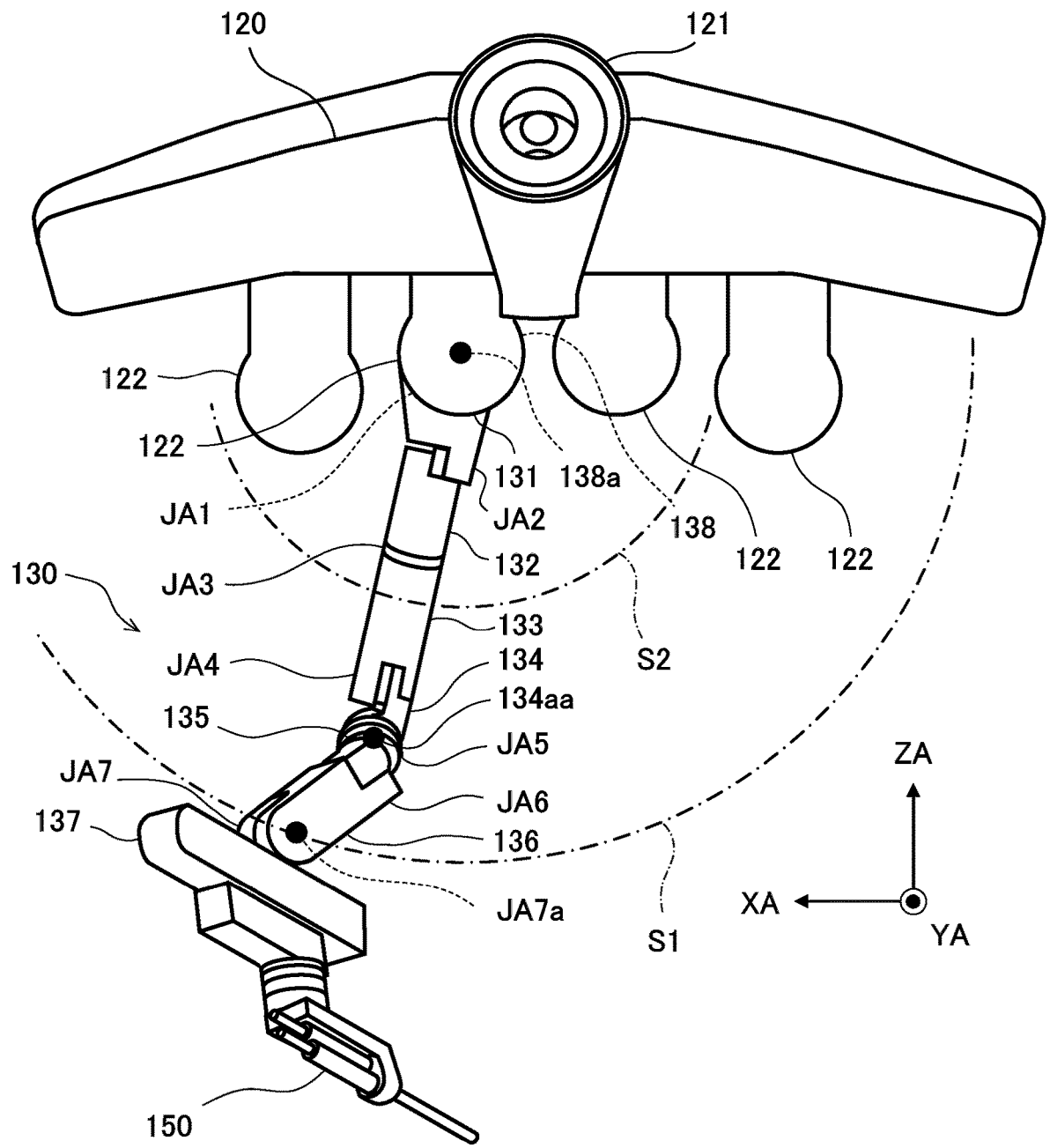
FIG. 9 is a side view showing another example of a restriction range in the same manner as FIG. 7.

Moreover, the restriction range may a three-dimensional region between the point 138a and a first curved surface defined with the point 138a as a reference point. Examples of the first curved surface include: a sphere like surface, such as a spherical surface or an oval spherical surface, whose center is the above reference point; and an axially symmetrical curved surface, such as a rotary curved surface, whose center is an axis passing through the above reference point. Examples of the above reference point include a center and a focal point. For example, as shown in FIG. 9, the first curved surface may be a spherical surface S1. The spherical surface S1 has the point 138a as its center and passes through the point JA7a. The restriction range may be an intermediate position between the point 138a and the first curved surface. For example, the restriction range may be an intermediate position between the point 138a and the spherical surface S1. FIG. 9 is a side view showing another example of the restriction range in the same manner as FIG. 7.

Moreover, the restriction range may be a region on a second curved surface between the point 138a and the first curved surface. The shape of the second curved surface may be similar to the shape of the first curved surface or may not be similar to the shape of the first curved surface. The second curved surface may be located at an intermediate position between the point 138a and the first curved surface. For example, as shown in FIG. 9, the second curved surface may be a spherical surface S2 between the point 138a and the spherical surface S1. The spherical surface S2 has the point 138a as its center but may have a point, which is different from the point 138a, as its center. The position of the spherical surface S2 may be between the point 138a and the spherical surface S1. For example, the position of the spherical surface S2 may be an intermediate position between the point 138a and the spherical surface S1.

Moreover, the restriction range may be a region on a line segment connecting the point 138a and the point JA7a, a region on a plane that passes through the above line segment and the YA axis, or a region on a plane that passes through the above line segment and the rotation axis of the joint JA1.

Moreover, each of the above regions on the planes and the above region on the line segment may denote a region near the plane or the line segment, such as a region within a predetermined distance from the plane or the line segment.

As described above, the restriction range of the bending point 134aa is a range that is determined so as to correspond to the position of the base link 138 and the position of the tip link 137 and changes so as to correspond to the position of the tip link 137. The following will be described on the basis that the restriction range is a two-dimensional region on the plane YZE located at the intermediate position between the plane YZ7 and the plane YZ8.

The image acquirer 311 acquires the image data taken by the endoscope camera as the surgical instrument 150 of the arm 130 and outputs the image data to the second control device 32.

The information processor 312 receives the manipulation operating command including the movement command, the force command, and the like from the second control device 32 and outputs the manipulation operating command to the operation commander 313. The information processor 312 may subject the manipulation operating command to processing and output the manipulation operating command to the operation commander 313. The information processor 312 reads the information of the constraint condition 31ca of the arm 130 as an operation target from the storage 31c based on, for example, a command, which is received from the second control device 32 and instructs execution of the restriction mode, and outputs the information of the constraint condition 31ca to the axis position determiner 314. The information processor 312 may subject the information of the constraint condition 31ca to processing and output the information of the constraint condition 31ca to the axis position determiner 314.

The operation commander 313 generates an operating command of the tip link 137 of the arm 130 as a target of the manipulation operating command from the manipulation operating command received from the information processor 312 and outputs the operating command to the axis position determiner 314. The operating command includes a position command and may further include a force command A preset movement range restriction, a preset movement speed restriction, and the like may be applied to the position command Moreover, the operation commander 313 receives operation information of the robot 10 from the operation controller 315, generates an operating command of the operating portions of the operation manipulators 211L and 211R by using the operation information, and outputs the operating command to the second control device 32. The operating command includes a position command and may further include a force command Instead of the operating command, the operation commander 313 may output the operation information of the robot 10 to the second control device 32.

The position command of the tip link 137 may include a command that instructs, for example, target values of the position, posture, position speed, and posture speed of the tip link 137 and/or target values of the positions, postures, position speeds, and posture speeds of the joints of the arm 130. The above position and the above position speed may respectively indicate a position and a speed within a three-dimensional space, and the above posture and the above posture speed may respectively indicate a posture and a speed within a three-dimensional space. Moreover, the position command may include an execution time of the position command. In the present description and the claims, the "position" denote at least the position within the three-dimensional space among the position, the position speed, the posture, and the posture speed within the three-dimensional space. The force command includes a command that instructs target values of the magnitude and direction of the force applied from the tip link 137 to the target object. The direction of the force may indicate a direction within a three-dimensional space. The force command may include an execution time of the force command Moreover, as with the position command of the tip link 137, the position command of the operating portions of the operation manipulators 211L and 211R may include a command that instructs, for example, target values of the positions, postures, position speeds, and posture speeds of the operating portions and/or target values of the positions, postures, position speeds, and posture speeds of the joints of the operation manipulators 211L and 211R. Furthermore, the position command may include an execution time of the position command. The force command may include a command that instructs target values of the magnitude and direction of the force applied to the operating portion. The force command may include an execution time of the force command The operation information of the robot 10 includes at least operation data of the arms 130 among operation data of the positioner 110 and the operation data of the arms 130. The operation data of the arm 130 includes, for example, position data indicating the position of the tip link 137 during operation and/or position data indicating the positions of the joints of the arm 130 during operation. The operation data of the arm 130 may include force data indicating the force applied from the tip link 137 to the target object. The operation data of the positioner 110 includes, for example, position data indicating the positions of the joints of the positioner 110 and/or the position of the arm base 120. The position data may include a position within a three-dimensional space and a posture within the three-dimensional space. The force data may include the magnitude of the force and the direction of the force within a three-dimensional space. The position data may be time-series data associated with a generated time of the position, and the force data may be time-series data associated with a generated time of the force.

Moreover, as information other than the operation data, the operation information may include, for example, taken image data of the target object to which action is applied by the tip link 137, and vibration data, impact data, optical data, sound data, temperature data, humidity data, and pressure data (such as atmospheric pressure) generated at the tip link 137. The operation information in the present embodiment includes at least the operation data.

Based on the operating command received from the operation commander 313, the axis position determiner 314 determines target values of the rotation amounts (rotation angles) of the joints JA1 to JA7 of the arm 130 as a target of the operating command and outputs the target values to the operation controller 315. To be specific, the axis position determiner 314 determines rotational positions of joint axes of the joints JA1 to JA7. Moreover, in the restriction mode, the axis position determiner 314 uses the constraint condition 31ca to determine the target values. The axis position determiner 314 may output the force command included in the operating command to the operation controller 315.

In each of the restriction mode and a non-restriction mode, the axis position determiner 314 performs inverse conversion using target values of a three-dimensional position and three-dimensional posture of the tip link 137, which are included in the position command of the operating command, and detected values of a three-dimensional position and three-dimensional posture of the base link 138, to calculate the target values of the rotation amounts (rotation angles) of the joints JA1 to JA7. The detected values of the three-dimensional position and three-dimensional posture of the base link 138 are calculated from the three-dimensional position and three-dimensional posture of the arm base 120. For example, after the arm base 120 is positioned by the positioner 110, the first control device 31 may detect and hold the three-dimensional position and three-dimensional posture of the arm base 120 and/or the three-dimensional position and three-dimensional posture of the base link 138 of the arm 130.

In the present embodiment, each arm 130 includes seven joints. Each arm 130 includes: six degrees of freedom realized by six joints necessary to set the three-dimensional position and three-dimensional posture of the tip link 137 to the target values; and one additional degree of freedom realized by one joint. Therefore, plural combinations of the rotation amounts (rotation angles) of the joints JA1 to JA7 may be detected by calculation with respect to one combination of the target values of the three-dimensional position and three-dimensional posture of the tip link 137.

In the non-restriction mode, the axis position determiner 314 selects an arbitrary combination from the plural combinations of the rotation amounts (rotation angles) of the joints JA1 to JA7 and determines the selected combination as the target values of the rotation amounts (rotation angles) of the joints JA1 to JA7. For example, the axis position determiner 314 may select a combination of shortest rotational movement amounts of the joints JA1 to JA7. For example, regarding the operation of the arm 130 based on the remote center position, the axis position determiner 314 may use the information of the remote center position in the above selection. From the combinations of the rotation amounts of the joints JA1 to JA7, the axis position determiner 314 may select a combination by which the surgical instrument 150 passes through the remote center position.

In the restriction mode, the axis position determiner 314 selects a combination of the rotation amounts (rotation angles) of the joints JA1 to JA7 by which the restriction portion of the arm 130 is located within the restriction range, based on the constraint condition 31ca and determines this combination as the target values. In the present embodiment, as shown in FIG. 7, the axis position determiner 314 selects a combination by which the bending point 134aa of the bent portion 134a of the link 134 is located on the plane YZE. The plane YZE is located at an intermediate position between the plane YZ7 passing through the point JA7a of the tip link 137 and perpendicular to the XA axis and the plane YZ8 passing through the point 138a of the base link 138 and perpendicular to the XA axis, and is parallel to the planes YZ7 and YZ8. For example, regarding the operation of the arm 130 based on the remote center position, the axis position determiner 314 may use the information of the remote center position in the above selection. From the combinations of the rotation amounts of the joints JA1 to JA7, the axis position determiner 314 may select a combination by which the surgical instrument 150 passes through the remote center position.

The operation controller 315 generates and outputs an operation control command of controlling the supply of the current to the servomotors MA1 to MA7 that respectively drive the joints JA1 to JA7 of the arm 130 as the operation target. Specifically, the operation controller 315 receives, as feedback information, the detected values of the rotation amounts from the rotation sensors EA1 to EA7 of the servomotors MA1 to MA7 and the detected values of the currents from current sensors (not shown) of the servomotors MA1 to MA7. The operation controller 315 may use, as the feedback information, the command values of the currents supplied from the driving circuits CA1 to CA7 to the servomotors MA1 to MA7. Moreover, when a force sensor is disposed at, for example, the tip link 137, the operation controller 315 may receive the detected value of the force as the feedback information from the force sensor. Furthermore, the operation controller 315 detects the positions of the joints JA1 to JA7 from the detected values of the rotation amounts of the joints JA1 to JA7. The operation controller 315 determines drive amounts and driving speeds of the joints JA1 to JA7 from the positions of the joints JA1 to JA7 and the target values of the rotation amounts (rotation angles) of the joints JA1 to JA7 received from the axis position determiner 314. Moreover, the operation controller 315 may determine driving torques of the joints JA1 to JA7 from the detected value of the force detected by the force sensor and the force command of the operating command. The operation controller 315 determines, based on the detected values of the currents, the current values by which the servomotors MA1 to MA7 drive so as to correspond to the drive amounts, the driving speeds, and the driving torques. Then, the operation controller 315 generates an operation control command of supplying the currents of the current values to the servomotors, and outputs the operation control command to the servomotors. With this, for example, when the arms 130 operate in accordance with the movement command of the manipulation operating command, the arms 130 operate so as to correspond to the movements of the operating portions of the operation manipulators 211L and 211R.

Operations of Surgical System

Figure 10:
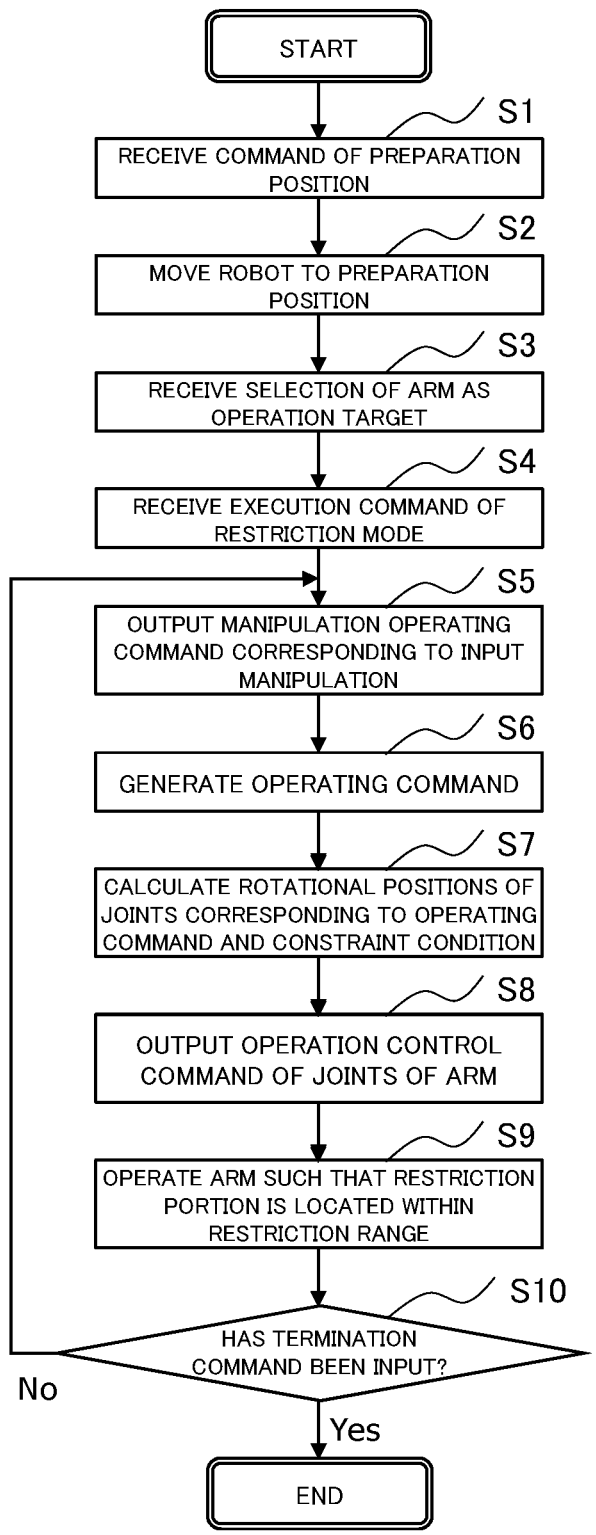
FIG. 10 is a flow chart showing one example of operations of the surgical system according to the embodiment.

The operations of the surgical system 1 according to the embodiment will be described. Specifically, the operations in the restriction mode will be described. FIG. 10 is a flow chart showing one example of the operations of the surgical system 1 according to the embodiment. As shown in FIG. 10, in Step S1, when performing surgery on the patient P, the surgeon S or the surgical assistant O inputs a command of specifying the preparation positions to the input device (not shown) of the robot 10, and the first control device 31 receives this command Next, in Step S2, the first control device 31 controls the positioner 110 and the like such that the positioner 110, the arm base 120, and the arms 130 are located at the specified preparation positions. The first control device 31 moves the robot 10 to the preparation position. After the movement to the preparation position, the surgical assistant O carries out the teaching of the remote center positions of the surgical instruments 150 when attaching the surgical instruments 150 to the arms 130A to 130D, and with this, the remote center positions Pa of the surgical instruments 150 are stored in the storage 31c.

Next, in Step S3, the surgeon S or the surgical assistant O uses the manipulation pedals 212 of the manipulation input device 210 to select the arm as the operation target operated by the operation manipulators 211L and 211R, among the arms 130A to 130D, and the second control device 32 receives this selection. In this example, the second control device 32 receives the selection of the arm 130C and outputs, to the first control device 31, notification that the arm 130C is the operation target. Thereafter, the first control device 31 processes, for example, a command from the second control device 32 as a command to the arm 130C.

Next, in Step S4, the surgeon S or the surgical assistant O inputs an execution command of the restriction mode to the manipulation input device 210. The second control device 32 receives the execution command of the restriction mode and outputs the command to the first control device 31.

Next, in Step S5, when the surgeon S inputs manipulation to the operating portions of the operation manipulators 211L and 211R, the second control device 32 generates the manipulation operating command corresponding to the manipulation and outputs the manipulation operating command to the first control device 31.

Next, in Step S6, the first control device 31 generates the operating command of the tip link 137 of the arm 130C from the manipulation operating command Next, in Step S7, the first control device 31 applies the remote center position Pa and the constraint condition 31ca, which are stored in the storage 31c, to the operating command With this, the first control device 31 calculates the target values of the rotation amounts (rotation angles) of the joints JA1 to JA7 of the arm 130C such that the bending point 134aa of the bent portion 134a of the link 134 of the arm 130C is located on the plane YZE (see FIG. 7) while maintaining a state where the surgical instrument 150 passes through the remote center position Pa. To be specific, the first control device 31 calculates the target values of the rotational positions of the joints JA1 to JA7 which values correspond to the operating command and the constraint condition 31ca.

Next, in Step S8, the first control device 31 acquires the operation information of the arm 130C. Moreover, the first control device 31 uses the operation information as the feedback information to generate the operation control command by which the joints JA1 to JA7 are operated such that the rotational positions thereof become the target values, and outputs the operation control command to the servomotors MA1 to MA7 of the arm 130C. To be specific, the first control device 31 outputs the operation control command of the joints JA1 to JA7 of the arm 130C.

Next, in Step S9, the arm 130C operates in accordance with the operation control command With this, the arm 130C moves the tip link 137 to the target position and the target posture while maintaining a state where the bending point 134aa of the link 134 is located on the plane YZE, and the surgical instrument 150 passes through the remote center position Pa. To be specific, the arm 130C operates such that the restriction portion is located within the restriction range.

Next, in Step S10, the second control device 32 determines whether or not the surgeon S or the surgical assistant O has inputted a termination command to the manipulation input device 210. When the command has been inputted (Yes in Step S10), the second control device 32 terminates the processing. When the command has not been inputted (No in Step S10), the second control device 32 returns to the processing of Step S5. The termination command may be a command that terminates the entire surgery of the surgical system 1, a command that terminates the restriction mode, a command that switches the operation target from the arm 130C to another arm 130, or the like.

In Steps S1 to S10, the first control device 31 moves the arm 130C such that the bending point 134aa of the link 134 which is the restriction portion of the arm 130C is located on the plane YZE that is the restriction range. With this, the joints JA1 to JA7 and the links 131 to 136 of the arm 130C operate within a range whose size is made small in directions toward the arms 130B and 130D located at both sides of the arm 130C. Therefore, the arm 130C is prevented from contacting the arms 130B and 130D. The first control device 31 can realize such operation of avoiding the contact of the arm 130C based on the state of the arm 130C, i.e., the state of the position of the point JA7a of the tip link 137 and the state of the position of the point 138a of the base link 138 without using the states of the arms 130B and 130D.

In the above embodiment, the arm 130C is the operation target. Even when another arm 130 is the operation target, the first control device 31 and the second control device 32 perform the same processing as Steps S3 to S10.

Moreover, in the above example, the restriction range is located on the plane YZE. However, even when the restriction range is another restriction range, the first control device 31 and the second control device 32 perform the same processing as Steps S5 to S10. Specifically, in Step S7, the first control device 31 calculates the target values of the rotational positions of the joints JA1 to JA7 of the arm 130 by using the constraint condition to be applied. The another restriction range may be the above-described restriction range.

Modified Example

An arm base 1200 of the robot 10 of the present modified example is different in configuration from the arm base 120 of the embodiment. Hereinafter, differences of the present modified example from the embodiment will be mainly described, and the same explanations as the embodiment will be suitably omitted.

Figure 11:
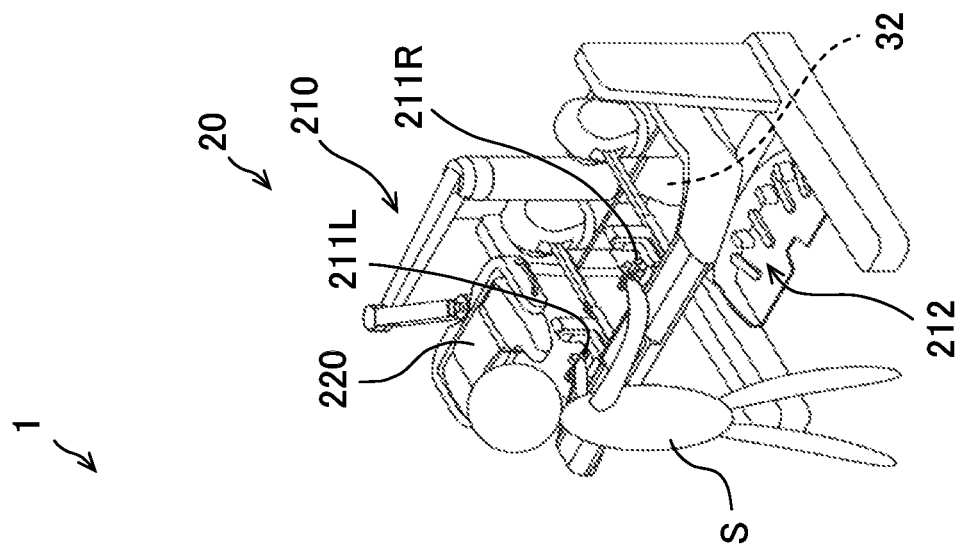
FIG. 11 is a diagram showing one example of the configuration of the surgical system according to Modified Example in the same manner as FIG. 1.
Figure 11:
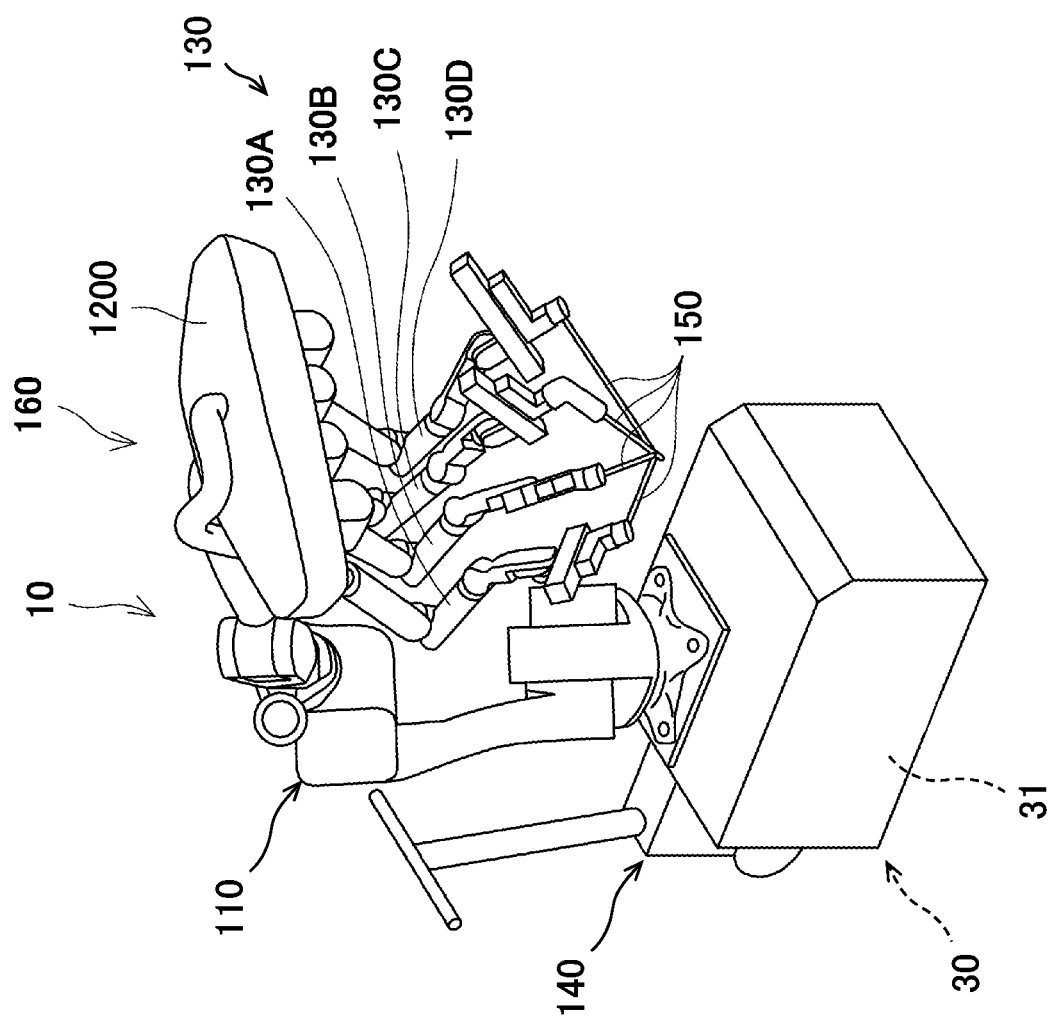
Figure 12:
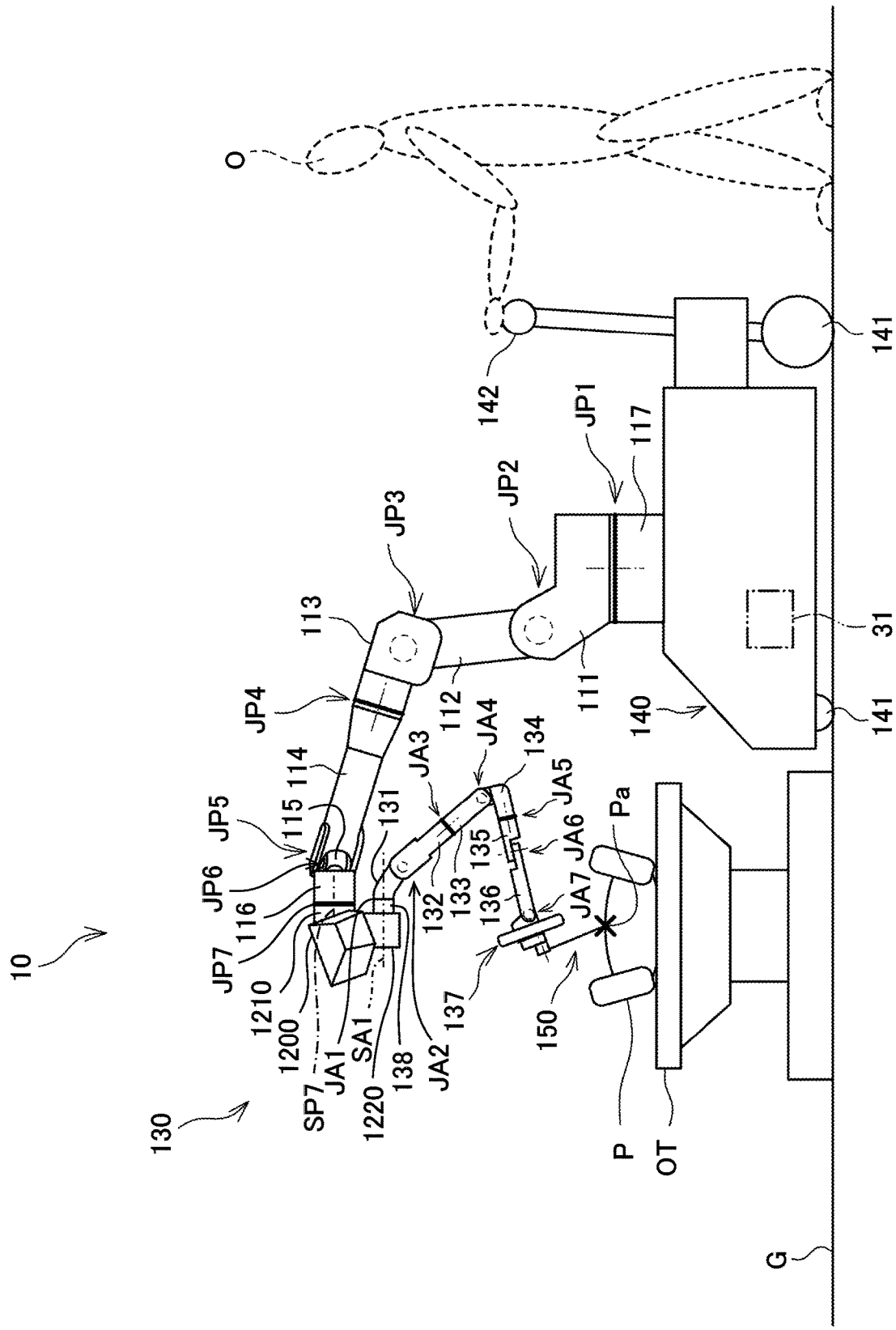
FIG. 12 is a side view showing one example of the configuration of the robot according to Modified Example in the same manner as FIG. 2.

FIG. 11 is a diagram showing one example of the configuration of the surgical system 1 according to the modified example in the same manner as FIG. 1. FIG. 12 is a side view showing one example of the configuration of the robot 10 according to the modified example in the same manner as FIG. 2. As shown in FIG. 1 and FIG. 2, the arm base 1200 of the robot 10 according to the present modified example includes a first attaching portion 1210 and a second attaching portion 1220.

The positioner link 116 of the positioner 110 is connected to the first attaching portion 1210 through the rotary joint JP7 and extends from the first attaching portion 1210 in a direction along the twist rotation axis SP7 of the rotary joint JP7.

The base link 138 of each arm 130 is connected to the second attaching portion 1220 and extends from the second attaching portion 1220 in a direction along the central axis SA1 where the second attaching portion 1220 extends. Based on the arm base 1200, a direction in which each base link 138 extends from the second attaching portion 1220 is the same as or similar to a direction in which the positioner link 116 extends from the first attaching portion 1210. To be specific, the direction of a mechanical interface of the first attaching portion 1210 is the same as or similar to the direction of each mechanical interface of the second attaching portion 1220. Therefore, the arms 130 and the positioner 110 extend in the same direction or similar directions from the arm base 1200. Moreover, the central axis SA1 and the rotation axis SP7 are parallel to each other in the present modified example, but the present modified example is not limited to this. Thus, the operations of the arms 130 and the positioner 110 are easily controlled.

The arm base 120 according to the embodiment is configured such that each arm 130 and the positioner 110 extend from the arm base 120 in respective directions substantially opposite to each other. The direction of a mechanical interface of the first attaching portion 121 of the arm base 120 is substantially opposite to the direction of each mechanical interface of the second attaching portion 122.

The first control device 31 performs the same control as the embodiment with respect to the robot 10 including the arm base 1200 described as above. Specifically, the first control device 31 performs the control by using the same constraint condition as the embodiment.

OTHER EMBODIMENTS

The foregoing has described the embodiment and the modified example of the present disclosure. However, the present disclosure is not limited to the above embodiment and the above modified example. To be specific, various modifications and improvements may be made within the scope of the present disclosure. For example, embodiments prepared by variously modifying the above embodiment and the above modified example and embodiments prepared by combining the components in the above embodiment and the above modified example are within the scope of the present disclosure.

For example, in the above embodiment and the above modified example, the point 134aa of the link 134 as the first portion of the first link of the arm 130 is located between the point 138a of the base link 138 as the second portion and the point JA7a of the tip link 137 as the third portion. However, the first portion, the second portion, and the third portion are not limited to the above. For example, the first portion may be any portion of the link 134 or any portion of one of the links 131 to 133 and 135 to 138. The second portion may be any portion of the base link 138 or any portion of one of the links 131 to 137. The third portion may be any portion of the tip link 137 or any portion of one of the links 131 to 136 and 138. The third portion may be located closer to the tip link 137 than the second portion, and the first portion may be located between the second portion and the third portion.

Moreover, the first to third portions may be located at the joints JA1 to JA7. For example, the first portion of the link 134 may be located at the joint JA4 or JA5 adjacent to the link 134. The second portion of the base link 138 may be located at the joint JA1 adjacent to the base link 138. The third portion of the tip link 137 may be located at the joint JA7 adjacent to the tip link 137. In the present description and the claims, the first portion of the first link (for example, the link 134) may be a portion in the first link or a portion in a joint (for example, the joint JA4 and/or the joint JA5) adjacent to the first link. The second portion of the base portion (for example, the base link 138) may be a portion in the base portion or a portion in a joint (for example, the joint JA1) adjacent to the base portion. The third portion of the tip portion (for example, the tip link 137) may be a portion in the tip portion or a portion in a joint (for example, the joint JA7) adjacent to the tip portion.

Moreover, the surgical system 1 according to each of the embodiment and the modified example includes one robot 10 and one console 20 but is not limited to this. The surgical system 1 may include one or more robots 10 and one or more consoles 20. For example, the surgical system 1 may include plural robots 10 and plural consoles 20. The control device 30 may select and connect one of the plural robots 10 and one of the plural consoles 20 in accordance with, for example, a command received from at least one of the plural consoles 20.

Moreover, the technology of the present disclosure may be a control method. For example, a control method according to the present disclosure is a method of controlling a surgical robot including an arm base, the arm base including robot arms, the robot arms each having plural degrees of freedom and including: a base portion; a tip portion that holds a medical instrument; and links that couple the base portion and the tip portion and are coupled to each other. At least one of the robot arms has at least seven degrees of freedom. The link adjacent to the base portion is connected to the base portion through a rotational joint. The method includes operating one robot arm having the at least seven degrees of freedom such that when viewed from a direction parallel to an axial direction of a rotation axis of the rotational joint, a first portion of a first link that is one of the links is located between a second portion of the base portion and a third portion of the tip portion. This control method can obtain the same effects as the above surgical system 1. This control method may be realized by a CPU, a circuit (such as an LSI), an IC card, a single module, or the like.

Moreover, the technology of the present disclosure may be a program for executing the above control method or may be a non-transitory, computer-readable recording medium that stores the above program. Moreover, needless to say, the above program is distributable through a transmission medium, such as the Internet.

Moreover, all the numerals, such as the ordinal numbers and the numbers, are examples used to specifically describe the technology of the present disclosure, and the present disclosure is not limited to these numerals. Furthermore, connection relations among the components are examples used to specifically describe the technology of the present disclosure, and the connection relations that realize the functions of the present disclosure are not limited to this.

Moreover, the division of the blocks in the functional block diagram is one example. Plural blocks may be realized as one block, one block may be divided into plural blocks, and/or some of the functions may be transferred to other blocks. Furthermore, the functions of plural blocks having similar functions may be processed by single hardware or software in parallel or in time division.

REFERENCE SIGNS LIST

1 surgical system
3 control device
10 robot
20 console
30 control device
31 first control device
32 second control device
120, 1200 arm base
130, 130A to 130D arm (robot arm)
131 to 136 link
134*aa* point (first portion)
137 tip link (tip portion)
138 base link (base portion)
138*a* point (second portion)
210 manipulation input device
JA7*a* point (third portion)

The invention claimed is:

1. A surgical robot comprising:
   robot arms each having plural degrees of freedom;
   an elongated arm base that holds base end portions of the robot arms; and
   a control device that controls movements of the robot arms, wherein:
   each of the robot arms includes
      a base portion,
      a tip portion that holds a medical instrument, and
      links that couple the base portion and the tip portion and are coupled to each other;
   the link adjacent to the base portion is connected to the base portion through a first rotational joint;
   the robot arms includes a first robot arm having at least seven degrees of freedom;
   the control device controls the first robot arm such that when viewed from a direction parallel to an axial direction of a rotation axis of the first rotational joint, a first portion of a first link that is one of the links is located between a second portion of the base portion and a third portion of the tip portion; and
   the control device controls the first robot arm such that the first portion is located between a first plane and a second plane, the first plane passing through the second portion and extending in a direction intersecting with a longitudinal direction of the arm base, the second plane passing through the third portion and extending in the direction intersecting with the longitudinal direction.

2. The surgical robot according to claim 1, wherein:
   the first link has a bent shape; and
   the first portion is a bent portion of the first link.

3. The surgical robot according to claim 1, wherein:
   the first link is connected to the base portion through two or more of the links; and
   the first link is connected to the tip portion through two or more of the links.

4. The surgical robot according to claim 1, wherein:
   the first plane passes through the second portion and extends in a direction perpendicular to the longitudinal direction; and
   the second plane passes through the third portion and extends in the direction perpendicular to the longitudinal direction.

5. The surgical robot according to claim 1, wherein the control device controls the first robot arm such that the first portion is located at an intermediate position between the first plane and the second plane.

6. A surgical system comprising:
   robot arms each having plural degrees of freedom;
   an elongated arm base that holds base end portions of the robot arms;
   a manipulation device by which at least one of the robot arms is manipulated; and
   a control device that controls movements of the robot arms based on manipulation of the manipulation device, wherein:
   the robot arms includes a first robot arm having at least seven degrees of freedom;
   each of the robot arms includes
      a base portion,
      a tip portion that holds a medical instrument, and
      links that couple the base portion and the tip portion and are coupled to each other;

the link adjacent to the base portion is connected to the base portion through a first rotational joint;

the control device moves the robot arm based on the manipulation of the manipulation device under such an operation restriction that the medical instrument is moved while maintaining a state where the medical instrument passes through a preset remote center position; and the control device controls the first robot arm manipulated by the manipulation device such that when viewed from a direction parallel to an axial direction of a rotation axis of the first rotational joint, a first portion of a first link that is one of the links is located between a second portion of the base portion and a third portion of the tip portion.

7. A method of controlling a surgical robot including an arm base, the arm base including robot arms, the robot arms each having plural degrees of freedom and including: a base portion; a tip portion that holds a medical instrument; and links that couple the base portion and the tip portion and are coupled to each other, wherein: the robot arms include a first robot arm having at least seven degrees of freedom; and the link adjacent to the base portion is connected to the base portion through a first rotational joint, the method comprising moving the first robot arm such that when viewed from a direction parallel to an axial direction of a rotation axis of the first rotational joint, a first portion of a first link that is one of the links is located between a second portion of the base portion and a third portion of the tip portion, wherein the first robot arm is operated such that the first portion is located between a first plane and a second plane, the first plane passing through the second portion and extending in a direction intersecting with a longitudinal direction of the arm base, the second plane passing through the third portion and extending in the direction intersecting with the longitudinal direction.

8. The method according to claim 7, wherein:
the first link is connected to the base portion through two or more of the links; and
the first link is connected to the tip portion through two or more of the links.

9. The method according to claim 7, wherein:
the first link has a bent shape; and
the first portion is a bent portion of the first link.

10. The method according to claim 7, wherein:
the first plane passes through the second portion and extends in a direction perpendicular to the longitudinal direction; and
the second plane passes through the third portion and extends in the direction perpendicular to the longitudinal direction.

11. The method according to claim 7, wherein the first robot arm is moved such that the first portion is located at an intermediate position between the first plane and the second plane.

12. The surgical robot according to claim 1, wherein:
the tip portion further includes
a linear motion mechanism that linearly moves the medical instrument,
a coupling portion, and
a second rotational joint connected to the linear motion mechanism through the coupling portion; and
the third portion of the tip portion is located at the second rotational joint.

13. The surgical system according to claim 6, wherein:
the first link has a bent shape; and
the first portion is a bent portion of the first link.

14. The surgical system according to claim 6, wherein:
the tip portion further includes
a linear motion mechanism that linearly moves the medical instrument,
a coupling portion, and
a second rotational joint connected to the linear motion mechanism through the coupling portion; and
the third portion of the tip portion is located at the second rotational joint.

15. The surgical system according to claim 6, wherein the control device controls the first robot arm such that the first portion is located between a first plane and a second plane, the first plane passing through the second portion and extending in a direction intersecting with a longitudinal direction of the arm base, the second plane passing through the third portion and extending in the direction intersecting with the longitudinal direction.

16. The surgical system according to claim 15, wherein:
the first plane passes through the second portion and extends in a direction perpendicular to the longitudinal direction; and
the second plane passes through the third portion and extends in the direction perpendicular to the longitudinal direction.

17. The surgical system according to claim 15, wherein the control device controls the first robot arm such that the first portion is located at an intermediate position between the first plane and the second plane.

18. The method according to claim 7, wherein:
the tip portion further includes
a linear motion mechanism that linearly moves the medical instrument,
a coupling portion, and
a second rotational joint connected to the linear motion mechanism through the coupling portion; and
the third portion of the tip portion is located at the second rotational joint.

* * * * *